US012606801B2

(12) United States Patent
Nicosia et al.

(10) Patent No.: US 12,606,801 B2
(45) Date of Patent: Apr. 21, 2026

(54) HERPESVIRUS WITH MODIFIED GLYCOPROTEIN H FOR PROPAGATION IN A CELL

(71) Applicant: ALMA MATER STUDIORUM UNIVERSITA DI BOLOGNA, Bologna (IT)

(72) Inventors: Alfredo Nicosia, Neapel (IT); Maria Gabriella Campadelli, Bologna (IT)

(73) Assignee: ALMA MATTER STUDIORUM UNIVERSITA DI BOLOGNA, Bologna (IT)

( * ) Notice: Subject to any disclaimer, the term of this patent is extended or adjusted under 35 U.S.C. 154(b) by 1238 days.

(21) Appl. No.: 16/307,708

(22) PCT Filed: Jun. 8, 2017

(86) PCT No.: PCT/EP2017/063949
§ 371 (c)(1),
(2) Date: Dec. 6, 2018

(87) PCT Pub. No.: WO2017/211945
PCT Pub. Date: Dec. 14, 2017

(65) Prior Publication Data
US 2019/0300862 A1      Oct. 3, 2019

(30) Foreign Application Priority Data
Jun. 9, 2016      (EP) ..................................... 16173831

(51) Int. Cl.
*C12N 7/00* (2006.01)
*A61K 35/763* (2015.01)
*C07K 14/005* (2006.01)

(52) U.S. Cl.
CPC .............. *C12N 7/00* (2013.01); *A61K 35/763* (2013.01); *C07K 14/005* (2013.01); *C07K 2319/00* (2013.01); *C12N 2710/16621* (2013.01); *C12N 2710/16622* (2013.01); *C12N 2710/16632* (2013.01); *C12N 2710/16652* (2013.01)

(58) Field of Classification Search
None
See application file for complete search history.

(56) References Cited

U.S. PATENT DOCUMENTS 8,980,282 B2 * 3/2015 Conner ................... A61P 35/00
424/235.1

FOREIGN PATENT DOCUMENTS

| WO | 2003/068809 | 8/2003 |
| WO | 2004/033639 | 4/2004 |
| WO | 2007/024668 | 3/2007 |
| WO | 2007/027774 | 3/2007 |
| WO | 2008/103762 | 8/2008 |
| WO | 2009013448 A2 | 1/2009 |
| WO | 2009/144755 | 12/2009 |
| WO | 2011/130749 | 10/2011 |
| WO | 2015/066042 | 5/2015 |
| WO | 2016/128497 | 8/2016 |

OTHER PUBLICATIONS

Klupp (Journal of Virology, vol. 73, No. 4, pp. 3014-3022). (Year: 1999).*
Weisser (Biotechnology Advances, 2009, vol. 27, pp. 502-520). (Year: 2009).*
Wainberg et al., Molecular Psychiatry, 2021, vol. 26, 5476-5480 (Year: 2021).*
Arii J. et al., "Non-Muscle Myosin IIA is a Functional Entry Receptor for Herpes Simplex Virus-1", Nature, 2010, 467, 859-862.
Arndt K. and Fin G.R., "GCN4 Protein, a Positive Transciption Factor in Yeast, Binds General Control Promoters at All 5' TGACTC 3' Sequences", PNAS 1986, 83, 8516-8520.
Backovic M. et al., "Structure of a Trimeric Variant of the Epstein-Barr Virus Glycoprotein B", PNAS, 2009, 106, 2880-2885.
Backovic M. et al., "Structure of a Core Fragment of Glycoprotein H from Pseudorabies Virus in Complex with Antibody", PNAS, 2010, 107, 22635-22640.
Bender F.C. et al., "Antigenic and Mutational Analyses of Herpes Simplex Virus Glycoprotein B Reveal Four Functional Regions", J Virol., 2007, 81, 3827-3841.
Burke H.G. and Heldwein E.E., "Crystal Structure of the Human Cytomegalovirus Glycoprotein B", PLOS Pathogens, 2015, 11, e1005227.
Burleson, F.G. et al., Virology: A Laboratory Manual, 1992, ISBN-13: 978-0121447304.
Castoldi R. et al., "Molecular Characterization of Novel Trispecific ErbB-cMet-IGFIR Antibodies and Their Antigen-Binding Properties", Protein Eng Des Sel, 2012, 25, 551-559.
Castoldi R. et al., "A Novel Bispecific EGFR/Met Antiboy Blocks Tumor-Promoting Phenotypic Effects Induced by Resistance to EGFR Inhibition and has Potent Antitumor Activity", Oncogene, 2013, 32, 5593-5601.
Chowdary T.K. et al., "Crystal Structure of the Conserved Herpesvirus Fusion Regulator Complex gH-gL", Nat Struct Mol Biol, 2010, 17, 882-888.

(Continued)

*Primary Examiner* — Celine X Qian
(74) *Attorney, Agent, or Firm* — STERNE, KESSLER, GOLDSTEIN & FOX P.L.L.C.

(57) ABSTRACT

The present invention is directed to a recombinant herpesvirus which comprises the GCN4 yeast transcription factor or a part thereof fused to or inserted into glycoprotein H and is capable of binding to a target molecule present on a cell for propagation and production of the herpesvirus. The herpesvirus may comprise additional modification in glycoprotein D and/or glycoprotein B for retargeting the herpesvirus to a diseased cell. The present invention is further directed to a nucleic acid and a vector coding for the gH, a polypeptide comprising the gH, and a cell comprising the herpesvirus, nucleic acid, vector or polypeptide. Moreover, the present invention is directed to a cell having accessible on the surface a target molecule for the GCN4 yeast transcription factor or part thereof and to a method for producing the herpesvirus in said cell.

19 Claims, 7 Drawing Sheets

Figure 1:
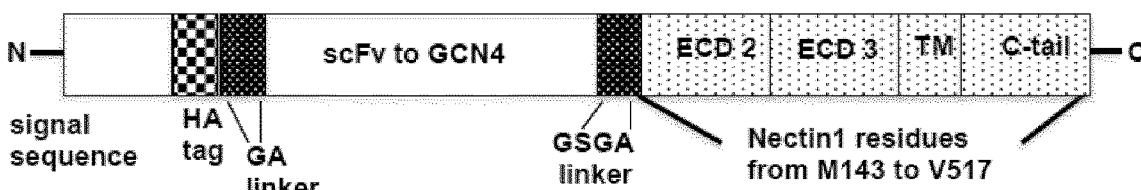

Specification includes a Sequence Listing.

(56) References Cited

OTHER PUBLICATIONS

Di Giovine P. et al., "Structure of Herpes Simplex Virus Glycoprotein D Bound to the Human Receptor Nectin-1", PLoS Pathogens 2011, 7,e1002277.

Gallagher J.R. et al., "Functional Fluorescent Protein Insertions in Herpes Simplex Virus gB Report on gB Conformation Before and After Execution of Membrane Fusion", PLoS Pathogens, 2014, 10, e1004373.

Gatta V. et al., Abstract # P-28, 9th International Conference on Oncolytic Virus Therapeutics, Boston 2015.

Heldwein E.E. et al., "Crystal Structure of Glycoprotein B from herpes Simplex Virus 1", Science, 2006, 313, 217-220.

Hope I.A. and Struhl K., "GCN4, a Eukaryotic Transcriptional Activator Protein, Binds as a Dimer to Target DNA", EMBO J, 1987, 6, 2781-2784.

Josan J.S. et al., "Cell-Specific Targeting by Heterobivalent Ligands", Bioconjug Chem, 2011, 22, 1270-1278.

Kamiyama H. et al., "Herpes Siplex Virus 1 Recombinant Virions Exhibiting the Amino Terminal Fragment of Urokinase-Type Plasminogen Activator can Enter Cells Via the Cognate Receptor", Gene Therapy, 2006, 13, 621-629.

Karlin S. and Altschul S.F., "Methods for Assessing the Statistical Significance of Molecular Sequence Features by Using General Scoring Schemes", PNAS, 1990, 87, 2264-2268.

Karlin S. and Altschul S.F., "Applications and Statistics for Multiple High-Scoring Segments in Molecular Sequences", PNAS, 1993, 90, 5873-5877.

Li W. et al., "Identification of Functional Domains in Herpes Simplex Virus 2 Glycoprotein B", J Virol, 2006, 80, 3792-3800.

Lin E. & Spear P.G., "Random Linker-Insertion Mutagenesis to Identify Functional Domains of Herpes Simplex Virus Type 1 Glycoprotein B", PNAS, 2007, 104, 13140-13145.

Liu B.L. et al., "ICP34.5 Deleted Herpes Simplex Virus with Enhanced Oncolytic, Immune Stimulating, and Anti-Tumour Properties", Gene Ther., 2003, 10, 292-303.

Matsuura H. et al., "Crystal Structure of the Epstein-Barr Virus (EBV) Glycoprotein H/Glycoprotein L (gH/gL) Complex", PNAS, 2010, 107, 22641-22646.

Menotti L et al., "Construction of a Fully Retargeted Herpes Simplex Virus 1 Recombinant Capable of Entering Cells Solely via Human Epidermal Growth Factor Receptor2", J Virol., 2008, 82, 10153-10161.

Menotti L. et al., "Inhibition of Human Tumor Growth in Mice by an Oncolytic Herpes Simplex Virus Designed to Target Solely HER-2-Positive Cells", PNAS, 2009, 106, 9039-9044.

Morgan A.A. and Rubenstein E., "Proline: The Distribution, Frequency, Positioning, and Common Functional Roles of Proline and Polyproline Sequences in the Human Proteome", PLoS One, 2013, 8, e53785.

Nakamura T. et al., "Rescue and Propagation of Fully Retargeted Oncolytic Measles Viruses", Nat Biotechnol, 2005, 23, 209-214.

Needleman S.B. and Wunsch C. D., "A General Method Applicable to the Search for Similarities in the Amino Acid Sequence of Two Proteins", J Mol Biol, 1970, 48, 443-453.

Pearson W.R. and Lipman D. J., "Improved Tools for Biological Sequence Comparison", PNAS, 1988, 85, 2444-2448.

Peterson R.B. and Goyal S.M., "Propagation and Quantitation of Animal Herpesviruses in Eight Cell Culture Systems", Comp Immunol Microbiol Infect Dis. 1988, 11, 93-98.

Petrovic B. et al., "Insertion of a Ligand to HER2 in gB Retargets HSV Tropism and Obviates the Need for Activaton of the Other Entry Glycoproteins", PLoS Pathogens, 2017, 13, e1006352.

Potel C. et al., "Incorporation of Green Fluorescent Protein into the Essential Envelope Glycoprotein B of Herpes Simplex Virus Type 1", J of Virological Methods, 2002, 105, 13-23.

Sandri-Goldin R.M., Alpha Herpesviruses: Molecular and Cellular Biology, Caister Academic Press, 2006.

Satoh T. et al., "PILRa is a Herpes Simplex Virus-1 Entry Co-Receptor that Associates with Glycoprotein B", Cell, 2008, 132, 935-944.

Shallal H.M. et al., "Heterobivalent Agents Targeting PSMA and Integrin-$\alpha_v\beta_{549}$ ,", Bioconjug Chem, 2014, 25, 393-405.

Shibata T. et al., "Development of an Oncolytic HSV Vector Fully Retargeted Specifically to Cellular EpCAM for Virus Entry and Cell-to-Cell Spread", Gene Therapy, 2016, 23, 479-488.

Smith T.F. and Waterman M.S., "Comparison of Biosequences", Add APL Math, 1981, 2, 482-489.

Suenaga T. et al., "Myelin-Associated Glycoprotein Mediates Membrane Fusion and Entry of Neurotropic Herpesviruses", PNAS 2010, 107, 866-871.

Uchida H. et al., "Effective Treatment of an Orthotopic Xenograft Model of Human Glioblastoma Using an EGFR-Retargeted Oncolytic Herpes Simplex Virus", Mol Ther, 2013, 21, 561-569.

Xu L. et al., "Heterobivalent Ligands Target Cell-Surface Receptor Combinations in Vivo", PNAS, 2012, 109, 21295-21300.

Zahnd C. et al., "Directed In Vitro Evolution and Crystallographic Analysis of a Peptide-Binding Single Chain Antibody Fragment (scFv) with Low Picomolar Affinity", J Biol Chem, 2004, 279, 18870-18877.

Zhou, G. et al., "Glycoprotein D or J Delivered in trans Blocks Apoptosis in SK—N—SH Cells Induced by a Herpes Simplex Virus 1 Mutant Lacking Intact Genes Expressing Both Glycoproteins", J Virol, 2000, 74, 11782-11791.

Zhou G. and Roizman B., "Characterization of a Recombinant Herpes Simplex Virus 1 Designed to Enter Cells via the IL13Rα2 Receptor of Malignant Glioma Cells", J Virol, 2005, 79, 5272-5277.

Avitabile, E. et al., "Complexes between Herpes Simplex Virus Glycoproteins gD, gB, and gH Detected in cells by Complementation of Split Enhanced Green Fluorescent Protein," Journal of Virology, vol. 81, No. 20, Aug. 1, 2007, pp. 11532-11537.

Cairns, T.M. et al., "Structure-Function Analysis of Herpes Simplex Virus Type 1 gD and gH-gL: Clues from gDgH Chimeras," Journal of Virology, vol. 77, No. 12, Jun. 15, 2003, pp. 6731-6742.

Douglas, J.T. et al., "A System for the Propagation of Adenoviral Vectors with Genetically Modified Receptor Specificities," Nature Biology, Gale Group, Inc., vol. 17, May 1, 1999, pp. 470-475.

Gatta, V. et al., "The Engineering of a Novel Ligand in gH Confers to HSV an Expanded Tropism Independent of gD Activation by Its Receptors," PLOS Pathogens, vol. 11, No. 5, May 21, 2015, pp. e1004907 (18 pages).

Leoni, V. et al., "A Strategy for Cultivation of Retargeted Oncolytic Herpes Simplex Viruses in Non-cancer Cells," Journal of Virology, vol. 91, No. 10, Mar. 1, 2017, pp. e00067-17 (13 pages).

Lorentzen, E.U. et al., "Replication-competent herpes simplex virus type 1 mutant expressing an autofluorescent glycoprotein H fusion protein," Intervirology, vol. 44, No. 4, Jan. 1, 2001, pp. 232-242.

International Search Report and Written Opinion for corresponding PCT/EP2017/063949, dated Oct. 25, 2017 (51 pages).

* cited by examiner

A

B

SEQUENCE LISTING

```
<160> NUMBER OF SEQ ID NOS: 20

<210> SEQ ID NO 1
<211> LENGTH: 838
<212> TYPE: PRT
<213> ORGANISM: Herpes simplex virus 1

<400> SEQUENCE: 1

Met Gly Asn Gly Leu Trp Phe Val Gly Val Ile Ile Leu Gly Val Ala
1               5                   10                  15

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
        35                  40                  45

Arg Leu Trp Leu Pro Asn Thr Pro Asp Pro Gln Lys Pro Pro Arg Gly
    50                  55                  60

Phe Leu Ala Pro Pro Asp Glu Leu Asn Leu Thr Thr Ala Ser Leu Pro
65                  70                  75                  80

Leu Leu Arg Trp Tyr Glu Glu Arg Phe Cys Phe Val Leu Val Thr Thr
                85                  90                  95

Ala Glu Phe Pro Arg Asp Pro Gly Gln Leu Leu Tyr Ile Pro Lys Thr
                100                 105                 110

Tyr Leu Leu Gly Arg Pro Pro Asn Ala Ser Leu Pro Ala Pro Thr Thr
            115                 120                 125

Val Glu Pro Thr Ala Gln Pro Pro Ser Val Ala Pro Leu Lys Gly
        130                 135                 140

Leu Leu Tyr Asn Pro Val Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
            180                 185                 190
```

-continued

```
Pro Pro Pro Arg Pro Pro Val Gly Ala Arg Arg His Pro Thr Thr Glu
        195             200             205

Leu Asp Ile Thr His Leu His Asn Ala Ser Thr Thr Trp Leu Ala Thr
        210             215             220

Arg Gly Leu Leu Arg Ser Pro Gly Arg Tyr Val Tyr Phe Ser Pro Ser
225             230             235             240

Ala Ser Thr Trp Pro Val Gly Ile Trp Thr Thr Gly Glu Leu Val Leu
            245             250             255

Gly Cys Asp Ala Ala Leu Val Arg Ala Arg Tyr Gly Arg Glu Phe Met
            260             265             270

Gly Leu Val Ile Ser Met His Asp Ser Pro Pro Val Glu Val Met Val
            275             280             285

Val Pro Ala Gly Gln Thr Leu Asp Arg Val Gly Asp Pro Ala Asp Glu
        290             295             300

Asn Pro Pro Gly Ala Leu Pro Gly Pro Pro Gly Gly Pro Arg Tyr Arg
305             310             315             320

Val Phe Val Leu Gly Ser Leu Thr Arg Ala Asp Asn Gly Ser Ala Leu
            325             330             335

Asp Ala Leu Arg Arg Val Gly Gly Tyr Pro Glu Glu Gly Thr Asn Tyr
            340             345             350

Ala Gln Phe Leu Ser Arg Ala Tyr Ala Glu Phe Phe Ser Gly Asp Ala
            355             360             365

Gly Ala Glu Gln Gly Pro Arg Pro Pro Leu Phe Trp Arg Leu Thr Gly
        370             375             380

Leu Leu Ala Thr Ser Gly Phe Ala Phe Val Asn Ala Ala His Ala Asn
385             390             395             400

Gly Ala Val Cys Leu Ser Asp Leu Leu Gly Phe Leu Ala His Ser Arg
            405             410             415

Ala Leu Ala Gly Leu Ala Ala Arg Gly Ala Ala Gly Cys Ala Ala Asp
            420             425             430

Ser Val Phe Phe Asn Val Ser Val Leu Asp Pro Thr Ala Arg Leu Gln
        435             440             445

Leu Glu Ala Arg Leu Gln His Leu Val Ala Glu Ile Leu Glu Arg Glu
        450             455             460

Gln Ser Leu Ala Leu His Ala Leu Gly Tyr Gln Leu Ala Phe Val Leu
465             470             475             480

Asp Ser Pro Ser Ala Tyr Asp Ala Val Ala Pro Ser Ala Ala His Leu
            485             490             495

Ile Asp Ala Leu Tyr Ala Glu Phe Leu Gly Gly Arg Val Leu Thr Thr
            500             505             510

Pro Val Val His Arg Ala Leu Phe Tyr Ala Ser Ala Val Leu Arg Gln
        515             520             525

Pro Phe Leu Ala Gly Val Pro Ser Ala Val Gln Arg Glu Arg Ala Arg
        530             535             540

Arg Ser Leu Leu Ile Ala Ser Ala Leu Cys Thr Ser Asp Val Ala Ala
545             550             555             560

Ala Thr Asn Ala Asp Leu Arg Thr Ala Leu Ala Arg Ala Asp His Gln
            565             570             575

Lys Thr Leu Phe Trp Leu Pro Asp His Phe Ser Pro Cys Ala Ala Ser
            580             585             590

Leu Arg Phe Asp Leu Asp Glu Ser Val Phe Ile Leu Asp Ala Leu Ala
            595             600             605

Gln Ala Thr Arg Ser Glu Thr Pro Val Glu Val Leu Ala Gln Gln Thr
```

```
            610              615              620
His Gly Leu Ala Ser Thr Leu Thr Arg Trp Ala His Tyr Asn Ala Leu
625              630              635              640

Ile Arg Ala Phe Val Pro Glu Ala Ser His Arg Cys Gly Gly Gln Ser
            645              650              655

Ala Asn Val Glu Pro Arg Ile Leu Val Pro Ile Thr His Asn Ala Ser
            660              665              670

Tyr Val Val Thr His Ser Pro Leu Pro Arg Gly Ile Gly Tyr Lys Leu
            675              680              685

Thr Gly Val Asp Val Arg Arg Pro Leu Phe Leu Thr Tyr Leu Thr Ala
            690              695              700

Thr Cys Glu Gly Ser Thr Arg Asp Ile Glu Ser Lys Arg Leu Val Arg
705              710              715              720

Thr Gln Asn Gln Arg Asp Leu Gly Leu Val Gly Ala Val Phe Met Arg
            725              730              735

Tyr Thr Pro Ala Gly Glu Val Met Ser Val Leu Leu Val Asp Thr Asp
            740              745              750

Asn Thr Gln Gln Gln Ile Ala Ala Gly Pro Thr Glu Gly Ala Pro Ser
            755              760              765

Val Phe Ser Ser Asp Val Pro Ser Thr Ala Leu Leu Leu Phe Pro Asn
            770              775              780

Gly Thr Val Ile His Leu Leu Ala Phe Asp Thr Gln Pro Val Ala Ala
785              790              795              800

Ile Ala Pro Gly Phe Leu Ala Ala Ser Ala Leu Gly Val Val Met Ile
            805              810              815

Thr Ala Ala Leu Ala Gly Ile Leu Lys Val Leu Arg Thr Ser Val Pro
            820              825              830

Phe Phe Trp Arg Arg Glu
            835
```

```
<210> SEQ ID NO 2
<211> LENGTH: 2577
<212> TYPE: DNA
<213> ORGANISM: Artificial sequence
<220> FEATURE:
<223> OTHER INFORMATION: Nucleotide sequence of chimeric gH-GCN4

<400> SEQUENCE: 2
atggggaatg gtttatggtt cgtggggggtt attattttgg gcgttgcgtg gggtcaggtc      60
cacgactggg gatccaagaa ctaccacctg gagaacgagg tggccagact gaagaagctg     120
gtgggcagca ctgagcagac agacccatgg tttttggatg gcctgggcat ggaccgcatg     180
tactggcgcg acacgaacac cgggcgtctg tggctgccaa acaccccccga cccccaaaaa     240 ccaccgcgcg gatttctggc gccgccggac gaactaaacc tgactacggc atctctgccc     300
cttcttcgct ggtacgagga gcgcttttgt tttgtattgg tcaccacggc cgagtttccg     360
cgggaccccg gccagctgct ttacatcccg aagacctacc tgctcggccg gccccgaac      420 gcgagcctgc cgcccccac acggtcgag ccgaccgccc agcctccccc ctcggtcgcc     480
ccccttaagg gtctcttgta caatccagtc gcctccgtgt tgctgcgttc ccgggcctgg     540
gtaacgtttt cggccgtccc tgaccccgag gccctgacgt tcccgcgggg agacaacgtg     600
gcgacggcga ccacccaag cgggccgcgt gatacaccgc cccccgacc gccggttggg      660 gccccggcggc accccgacgac ggagctggac atcacgcacc tgcacaacgc gtccacgacc     720
tggttggcca cccgggggcct gttgagatcc ccaggtaggt acgtgtattt ctccccgtcg     780
```

-continued

```
gcctcgacgt ggcccgtggg catctggacg acgggggagc tggtgctcgg gtgcgatgcc      840
gcgctggtgc gcgcgcgcta cgggcgggaa ttcatggggc tcgtgatatc catgcacgac      900
agccctccgg tggaagtgat ggtggtcccc gcgggccaga cgctagatcg ggtcggggac      960
cccgcggacg aaaacccccc gggggctctt cccgggcccc cgggcgggccc ccggtatcgg     1020 gtctttgtcc tagggtccct gacgcgggcc gacaacggct ccgcgctgga cgccctccgc     1080
cgcgtgggcg gctacccgga ggagggcacg aactacgccc agttcctgtc gcgggcatac     1140
gcggagtttt tctcggggga cgcgggcgcc gagcagggcc cgcgcccccc tctcttctgg     1200
cgcctaacgg ggctgctcgc gacgtcgggt tttgctttcg tgaacgccgc ccacgcaaac     1260
ggcgcggtct gcctctccga cctgctaggc tttttggccc actcgcgcgc gcttgccggg     1320
ttggccgccc gcggggccgc gggctgtgcc gcggattctg tgtttttaa tgtgtcagtc      1380 ttggatccca cggcccgcct gcagctagag gctcggctcc agcacctggt ggccgagatt     1440
ctggagcgcg aacagagctt ggcattacac gcgctgggcg atcagctggc cttcgtgctg     1500
gatagcccct cggcgtacga cgcagtggcg cccagcgcag cccatctcat cgacgccctg     1560
tatgccgagt ttctaggggg ccgcgtgctg accaccccgg tcgtccaccg ggcgctattt     1620
tacgcctcgg ctgtcctccg gcagccgttc ttggcgggcg tcccctcggc ggtgcagcgg     1680
gaacgcgccc gccggagcct tctgatagca tcggccctgt gtacgtccga cgtcgccgca     1740
gcgaccaacg ccgacctccg gaccgcgctg gcccgggccg accaccagaa aaccctcttt     1800
tggcttccgg accactttttc gccatgcgcg gcctccctgc gctttgatct agacgagagc     1860
gtgtttatcc tggacgcgct ggctcaagcc acccgatccg agaccccggt cgaagtcctg     1920
gcccagcaga cccacggcct cgcctcgacc ctgacgcgct gggcacacta caacgccctg     1980
atccgcgcct tcgtccctga ggcctcacat cggtgcgggg ggcagtctgc caacgtcgag     2040
ccacggatcc tggtacccat cacccacaac gccagctacg tcgtcaccca ctcccctctg     2100
ccccggggga tcggctacaa gctcaccggc gtcgacgtcc gacgcccact gttcctaacc     2160
tacctcaccg cgacatgcga aggctccacc cgggatatcg agtccaagcg gctggtgcgc     2220
acccaaaacc agcgcgacct ggggctcgtg ggggccgtgt ttatgcgcta caccccagcc     2280
ggggaggtca tgtctgtgtt gctggtggat acggacaaca cacagcagca aatcgccgcc     2340
gggccgacgg agggcgcccc gagcgtgttt tcgagcgacg tgccgtccac ggccttgttg     2400
ctatttccaa acggaaccgt cattcatttg ctagcctttg acacgcagcc cgtggccgca     2460
attgcgcccg ggtttctggc cgcctctgcg ctggcgtgg ttatgattac cgccgccctg      2520
gctggcatcc taaaggttct ccggacaagt gtcccgtttt tttggagacg cgaataa        2577
```

<210> SEQ ID NO 3
<211> LENGTH: 858
<212> TYPE: PRT
<213> ORGANISM: Artificial sequence
<220> FEATURE:
<223> OTHER INFORMATION: Amino acid sequence of gH precursor (SEQ ID NO:
      1) having inserted the GCN4 peptide between amino acids 23 and 24

<400> SEQUENCE: 3

```
Met Gly Asn Gly Leu Trp Phe Val Gly Val Ile Ile Leu Gly Val Ala
1               5                   10                  15

Trp Gly Gln Val His Asp Trp Gly Ser Lys Asn Tyr His Leu Glu Asn
            20                  25                  30

Glu Val Ala Arg Leu Lys Lys Leu Val Gly Ser Thr Glu Gln Thr Asp
```

-continued

```
                 35                      40                      45

Pro Trp Phe Leu Asp Gly Leu Gly Met Asp Arg Met Tyr Trp Arg Asp
    50                      55                      60

Thr Asn Thr Gly Arg Leu Trp Leu Pro Asn Thr Pro Asp Pro Gln Lys
65                      70                      75                      80

Pro Pro Arg Gly Phe Leu Ala Pro Pro Asp Glu Leu Asn Leu Thr Thr
                85                      90                      95

Ala Ser Leu Pro Leu Leu Arg Trp Tyr Glu Glu Arg Phe Cys Phe Val
            100                     105                     110

Leu Val Thr Thr Ala Glu Phe Pro Arg Asp Pro Gly Gln Leu Leu Tyr
            115                     120                     125

Ile Pro Lys Thr Tyr Leu Leu Gly Arg Pro Pro Asn Ala Ser Leu Pro
    130                     135                     140

Ala Pro Thr Thr Val Glu Pro Thr Ala Gln Pro Pro Ser Val Ala
145                     150                     155                     160

Pro Leu Lys Gly Leu Leu Tyr Asn Pro Val Ala Ser Val Leu Leu Arg
            165                     170                     175

Ser Arg Ala Trp Val Thr Phe Ser Ala Val Pro Asp Pro Glu Ala Leu
            180                     185                     190

Thr Phe Pro Arg Gly Asp Asn Val Ala Thr Ala Ser His Pro Ser Gly
            195                     200                     205

Pro Arg Asp Thr Pro Pro Pro Arg Pro Pro Val Gly Ala Arg Arg His
    210                     215                     220

Pro Thr Thr Glu Leu Asp Ile Thr His Leu His Asn Ala Ser Thr Thr
225                     230                     235                     240

Trp Leu Ala Thr Arg Gly Leu Leu Arg Ser Pro Gly Arg Tyr Val Tyr
            245                     250                     255

Phe Ser Pro Ser Ala Ser Thr Trp Pro Val Gly Ile Trp Thr Thr Gly
            260                     265                     270

Glu Leu Val Leu Gly Cys Asp Ala Ala Leu Val Arg Ala Arg Tyr Gly
            275                     280                     285

Arg Glu Phe Met Gly Leu Val Ile Ser Met His Asp Ser Pro Pro Val
    290                     295                     300

Glu Val Met Val Val Pro Ala Gly Gln Thr Leu Asp Arg Val Gly Asp
305                     310                     315                     320

Pro Ala Asp Glu Asn Pro Pro Gly Ala Leu Pro Gly Pro Pro Gly Gly
            325                     330                     335

Pro Arg Tyr Arg Val Phe Val Leu Gly Ser Leu Thr Arg Ala Asp Asn
            340                     345                     350

Gly Ser Ala Leu Asp Ala Leu Arg Arg Val Gly Gly Tyr Pro Glu Glu
            355                     360                     365

Gly Thr Asn Tyr Ala Gln Phe Leu Ser Arg Ala Tyr Ala Glu Phe Phe
    370                     375                     380

Ser Gly Asp Ala Gly Ala Glu Gln Gly Pro Arg Pro Pro Leu Phe Trp
385                     390                     395                     400

Arg Leu Thr Gly Leu Leu Ala Thr Ser Gly Phe Ala Phe Val Asn Ala
                405                     410                     415

Ala His Ala Asn Gly Ala Val Cys Leu Ser Asp Leu Leu Gly Phe Leu
            420                     425                     430

Ala His Ser Arg Ala Leu Ala Gly Leu Ala Ala Arg Gly Ala Ala Gly
            435                     440                     445

Cys Ala Ala Asp Ser Val Phe Phe Asn Val Ser Val Leu Asp Pro Thr
    450                     455                     460
```

-continued

```
Ala Arg Leu Gln Leu Glu Ala Arg Leu Gln His Leu Val Ala Glu Ile
465                 470                 475                 480

Leu Glu Arg Glu Gln Ser Leu Ala Leu His Ala Leu Gly Tyr Gln Leu
                485                 490                 495

Ala Phe Val Leu Asp Ser Pro Ser Ala Tyr Asp Ala Val Ala Pro Ser
            500                 505                 510

Ala Ala His Leu Ile Asp Ala Leu Tyr Ala Glu Phe Leu Gly Gly Arg
            515                 520                 525

Val Leu Thr Thr Pro Val Val His Arg Ala Leu Phe Tyr Ala Ser Ala
        530                 535                 540

Val Leu Arg Gln Pro Phe Leu Ala Gly Val Pro Ser Ala Val Gln Arg
545                 550                 555                 560

Glu Arg Ala Arg Arg Ser Leu Leu Ile Ala Ser Ala Leu Cys Thr Ser
                565                 570                 575

Asp Val Ala Ala Ala Thr Asn Ala Asp Leu Arg Thr Ala Leu Ala Arg
            580                 585                 590

Ala Asp His Gln Lys Thr Leu Phe Trp Leu Pro Asp His Phe Ser Pro
            595                 600                 605

Cys Ala Ala Ser Leu Arg Phe Asp Leu Asp Glu Ser Val Phe Ile Leu
        610                 615                 620

Asp Ala Leu Ala Gln Ala Thr Arg Ser Glu Thr Pro Val Glu Val Leu
625                 630                 635                 640

Ala Gln Gln Thr His Gly Leu Ala Ser Thr Leu Thr Arg Trp Ala His
                645                 650                 655

Tyr Asn Ala Leu Ile Arg Ala Phe Val Pro Glu Ala Ser His Arg Cys
            660                 665                 670

Gly Gly Gln Ser Ala Asn Val Glu Pro Arg Ile Leu Val Pro Ile Thr
            675                 680                 685

His Asn Ala Ser Tyr Val Val Thr His Ser Pro Leu Pro Arg Gly Ile
        690                 695                 700

Gly Tyr Lys Leu Thr Gly Val Asp Val Arg Arg Pro Leu Phe Leu Thr
705                 710                 715                 720

Tyr Leu Thr Ala Thr Cys Glu Gly Ser Thr Arg Asp Ile Glu Ser Lys
                725                 730                 735

Arg Leu Val Arg Thr Gln Asn Gln Arg Asp Leu Gly Leu Val Gly Ala
            740                 745                 750

Val Phe Met Arg Tyr Thr Pro Ala Gly Glu Val Met Ser Val Leu Leu
            755                 760                 765

Val Asp Thr Asp Asn Thr Gln Gln Ile Ala Ala Gly Pro Thr Glu
        770                 775                 780

Gly Ala Pro Ser Val Phe Ser Ser Asp Val Pro Ser Thr Ala Leu Leu
785                 790                 795                 800

Leu Phe Pro Asn Gly Thr Val Ile His Leu Leu Ala Phe Asp Thr Gln
                805                 810                 815

Pro Val Ala Ala Ile Ala Pro Gly Phe Leu Ala Ala Ser Ala Leu Gly
            820                 825                 830

Val Val Met Ile Thr Ala Ala Leu Ala Gly Ile Leu Lys Val Leu Arg
            835                 840                 845

Thr Ser Val Pro Phe Phe Trp Arg Arg Glu
            850                 855
```

<210> SEQ ID NO 4
<211> LENGTH: 822

```
<212> TYPE: DNA
<213> ORGANISM: Artificial sequence
<220> FEATURE:
<223> OTHER INFORMATION: Nucleotide sequence of scFv to GCN4 peptide
      preceded by 96 nucleotide that form the signal sequence and the HA
      tag

<400> SEQUENCE: 4
atggaaaccg acacccttct tttgtgggtg cttcttcttt gggtgcccgg gagcaccggg      60
gactacccct acgacgtgcc cgactacgcc ggggctgatg ccgtggtgac ccaggagagc     120
gccttgacca caagcccggg ggagaccgtg accttgacct gtagaagcag cacaggggcc     180
gttacaacct ctaactacgc cagctgggtt caggagaagc ccgaccacct tttcaccgga     240
cttatcggag ggaccaacaa cagagccccc ggggtgcctg ctagattcag cgggagcctt     300
attggggaca aggccgccct taccattacc ggggctcaga ccgaagacga ggctatctac     360
ttctgtgctc tttggtacag caaccattgg gtgttcggag gcgggacaaa gcttacagtg     420 cttgaggcg gtggaggcag cggcggaggt gggtctggtg gaggggctc tgggggaggc      480 ggtagcgacg tgcagcttca gcagagcggg cccgggcttg tggccccctc tcagtctctt     540
agcataacgt gcaccgtgag cgggttcagc cttaccgact atgggggttaa ctgggtgaga    600 cagtctcctg ggaaggggct tgagtggttg ggagttatct ggggagacgg aatcaccgac     660
tacaacagcg ccttgaagag cagactttct gtgacaaagg acaactctaa gagccaggtg     720
ttccttaaga tgaacagcct tcagagcggg gactctgcca gatactactg cgtgacaggg     780
cttttcgact actggggaca agggaccacc ttgaccgtga gc                         822

<210> SEQ ID NO 5
<211> LENGTH: 275
<212> TYPE: PRT
<213> ORGANISM: Artificial sequence
<220> FEATURE:
<223> OTHER INFORMATION: Amino acid sequence of scFv to GCN4 peptide
      preceded by 32 AA that constitute the signal sequence and the HA
      tag

<400> SEQUENCE: 5

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Asp Ala Val Val Thr Gln Glu Ser Ala Leu Thr Thr Ser Pro Gly Glu
        35                  40                  45

Thr Val Thr Leu Thr Cys Arg Ser Ser Thr Gly Ala Val Thr Thr Ser
    50                  55                  60

Asn Tyr Ala Ser Trp Val Gln Glu Lys Pro Asp His Leu Phe Thr Gly
65                  70                  75                  80

Leu Ile Gly Gly Thr Asn Asn Arg Ala Pro Gly Val Pro Ala Arg Phe
                85                  90                  95

Ser Gly Ser Leu Ile Gly Asp Lys Ala Ala Leu Thr Ile Thr Gly Ala
            100                 105                 110

Gln Thr Glu Asp Glu Ala Ile Tyr Phe Cys Ala Leu Trp Tyr Ser Asn
        115                 120                 125

His Trp Val Phe Gly Gly Gly Thr Lys Leu Thr Val Leu Gly Gly Gly
    130                 135                 140

Gly Gly Ser Gly Gly Gly Gly Ser Gly Gly Gly Gly Ser Gly Gly Gly
145                 150                 155                 160
```

```
Gly Ser Asp Val Gln Leu Gln Gln Ser Gly Pro Gly Leu Val Ala Pro
                165                 170                 175

Ser Gln Ser Leu Ser Ile Thr Cys Thr Val Ser Gly Phe Ser Leu Thr
            180                 185                 190

Asp Tyr Gly Val Asn Trp Val Arg Gln Ser Pro Gly Lys Gly Leu Glu
        195                 200                 205

Trp Leu Gly Val Ile Trp Gly Asp Gly Ile Thr Asp Tyr Asn Ser Ala
    210                 215                 220

Leu Lys Ser Arg Leu Ser Val Thr Lys Asp Asn Ser Lys Ser Gln Val
225                 230                 235                 240

Phe Leu Lys Met Asn Ser Leu Gln Ser Gly Asp Ser Ala Arg Tyr Tyr
                245                 250                 255

Cys Val Thr Gly Leu Phe Asp Tyr Trp Gly Gln Gly Thr Thr Leu Thr
                260                 265                 270

Val Ser Ser
        275
```

<210> SEQ ID NO 6
<211> LENGTH: 1964
<212> TYPE: DNA
<213> ORGANISM: Artificial sequence
<220> FEATURE:
<223> OTHER INFORMATION: Nucleotide sequence of scFv-GCN4 Nectin1
      chimera

<400> SEQUENCE: 6

```
atggaaaccg acacccttct tttgtgggtg cttcttcttt gggtgcccgg gagcaccggg        60
gactacccct acgacgtgcc cgactacgcc ggggctgatg ccgtggtgac ccaggagagc       120
gccttgacca caagccccgg ggagaccgtg accttgacct gtagaagcag cacagggggcc      180 gttacaacct ctaactacgc cagctgggtt caggagaagc ccgaccacct tttcaccgga       240
cttatcggag ggaccaacaa cagagccccc ggggtgcctg ctagattcag cgggagcctt       300 attgggggaca aggccgccct taccattacc ggggctcaga ccgaagacga ggctatctac      360
ttctgtgctc tttggtacag caaccattgg gtgttcggag gcgggacaaa gcttacagtg       420
cttggaggcg tggaggcag cggcggaggt gggtctggtg gaggggggctc tggggggaggc      480 ggtagcgacg tgcagcttca gcagagcggg cccgggcttg tggcccccctc tcagtctctt      540 agcataacgt gcaccgtgag cgggttcagc cttaccgact atggggttaa ctgggtgaga       600
cagtctcctg gaaggggggct tgagtggttg ggagttatct ggggagacgg aatcaccgac      660
tacaacagcg ccttgaagag cagactttct gtgacaaagg acaactctaa gagccaggtg       720
ttccttaaga tgaacagcct tcagagcggg gactctgcca gatactactg cgtgacaggg       780 ctttttcgact actggggaca aggaccacc ttgaccgtga gcagcggaag cggagccatg       840 gccaagcccca ccaactggat cgaggggaca caggccgtgc ttagagccaa gaaggggcag      900
gacgacaagg ttcttgttgc tacttgcacc agcgccaacg aaagcccccc cagcgtggtg       960
agctgggaga caagattgaa aggggaggcc gagtatcagg agatcagaaa ccctaacggg      1020
accgtgaccg tgatcagcag atacagactt gtgcctagca gagaggccca ccagcagagc      1080
cttgcctgca tcgttaacta ccacatggac agattcaagg agagccttac acttaacgtg      1140
cagtacgaac ccgaggtgac catcgagggg ttcgacggga actggtacct tcagagaatg      1200
gacgtgaagc ttacctgcaa ggccgacgcc aaccctcccg ccaccgagta ccactggacc      1260 accccttaacg ggagccttcc caaagggggtg gaggcccaga acagaaccct tttcttcaag     1320
```

-continued

```
gggcccatca attacagcct tgccgggacc tacatctgcg aggccaccaa ccccatcggg   1380
accagaagcg gtcaagtgga ggtgaacatc accgagttcc cctacacccc cagcccaccc   1440
gagcacggga gaagagctgg gcccgttccc accgccatca tcggaggggt ggccgggagc   1500
atcttgcttg tgcttatcgt ggtgggtggg attgtggtgg cccttagaag aagaagacat   1560
accttcaaag gggactacag caccaagaag cacgtgtacg ggaacgggta cagcaaggcc   1620
ggaatccctc agcaccatcc acctatggcc cagaaccttc agtaccccga cgacagcgac   1680
gatgagaaga aggctgggcc ccttggtggg agcagctacg aagaggagga agaagaggaa   1740
gagggtggcg gcggtggaga gagaaaagtg ggagggcctc atcccaaata cgacgaggac   1800
gccaagagac cctacttcac cgtggacgag gccgaggcca gacaggacgg gtacggggac   1860
agaacccttg ggtaccagta cgaccccgag cagttggact tggccgagaa catggtgagc   1920
cagaacgacg gaagcttcat ctctaagaag gagtggtacg tgtg           1964
```

```
<210> SEQ ID NO 7
<211> LENGTH: 654
<212> TYPE: PRT
<213> ORGANISM: Artificial sequence
<220> FEATURE:
<223> OTHER INFORMATION: Amino acid sequence of scFv-GCN4 Nectin1
      chimera

<400> SEQUENCE: 7

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Asp Ala Val Val Thr Gln Glu Ser Ala Leu Thr Thr Ser Pro Gly Glu
        35                  40                  45

Thr Val Thr Leu Thr Cys Arg Ser Ser Thr Gly Ala Val Thr Thr Ser
    50                  55                  60

Asn Tyr Ala Ser Trp Val Gln Glu Lys Pro Asp His Leu Phe Thr Gly
65                  70                  75                  80

Leu Ile Gly Gly Thr Asn Asn Arg Ala Pro Gly Val Pro Ala Arg Phe
                85                  90                  95

Ser Gly Ser Leu Ile Gly Asp Lys Ala Ala Leu Thr Ile Thr Gly Ala
            100                 105                 110

Gln Thr Glu Asp Glu Ala Ile Tyr Phe Cys Ala Leu Trp Tyr Ser Asn
        115                 120                 125

His Trp Val Phe Gly Gly Gly Thr Lys Leu Thr Val Leu Gly Gly Gly
    130                 135                 140

Gly Gly Ser Gly Gly Gly Gly Ser Gly Gly Gly Gly Ser Gly Gly Gly
145                 150                 155                 160

Gly Ser Asp Val Gln Leu Gln Gln Ser Gly Pro Gly Leu Val Ala Pro
                165                 170                 175

Ser Gln Ser Leu Ser Ile Thr Cys Thr Val Ser Gly Phe Ser Leu Thr
            180                 185                 190

Asp Tyr Gly Val Asn Trp Val Arg Gln Ser Pro Gly Lys Gly Leu Glu
        195                 200                 205

Trp Leu Gly Val Ile Trp Gly Asp Gly Ile Thr Asp Tyr Asn Ser Ala
    210                 215                 220

Leu Lys Ser Arg Leu Ser Val Thr Lys Asp Asn Ser Lys Ser Gln Val
225                 230                 235                 240

Phe Leu Lys Met Asn Ser Leu Gln Ser Gly Asp Ser Ala Arg Tyr Tyr
```

-continued

```
              245            250            255

Cys Val Thr Gly Leu Phe Asp Tyr Trp Gly Gln Gly Thr Thr Leu Thr
              260            265            270

Val Ser Ser Gly Ser Gly Ala Met Ala Lys Pro Thr Asn Trp Ile Glu
              275            280            285

Gly Thr Gln Ala Val Leu Arg Ala Lys Lys Gly Gln Asp Asp Lys Val
          290            295            300

Leu Val Ala Thr Cys Thr Ser Ala Asn Gly Lys Pro Pro Ser Val Val
305            310            315            320

Ser Trp Glu Thr Arg Leu Lys Gly Glu Ala Glu Tyr Gln Glu Ile Arg
              325            330            335

Asn Pro Asn Gly Thr Val Thr Val Ile Ser Arg Tyr Arg Leu Val Pro
              340            345            350

Ser Arg Glu Ala His Gln Gln Ser Leu Ala Cys Ile Val Asn Tyr His
              355            360            365

Met Asp Arg Phe Lys Glu Ser Leu Thr Leu Asn Val Gln Tyr Glu Pro
          370            375            380

Glu Val Thr Ile Glu Gly Phe Asp Gly Asn Trp Tyr Leu Gln Arg Met
385            390            395            400

Asp Val Lys Leu Thr Cys Lys Ala Asp Ala Asn Pro Pro Ala Thr Glu
              405            410            415

Tyr His Trp Thr Thr Leu Asn Gly Ser Leu Pro Lys Gly Val Glu Ala
              420            425            430

Gln Asn Arg Thr Leu Phe Phe Lys Gly Pro Ile Asn Tyr Ser Leu Ala
          435            440            445

Gly Thr Tyr Ile Cys Glu Ala Thr Asn Pro Ile Gly Thr Arg Ser Gly
          450            455            460

Gln Val Glu Val Asn Ile Thr Glu Phe Pro Tyr Thr Pro Ser Pro Pro
465            470            475            480

Glu His Gly Arg Arg Ala Gly Pro Val Pro Thr Ala Ile Ile Gly Gly
              485            490            495

Val Ala Gly Ser Ile Leu Leu Val Leu Ile Val Val Gly Gly Ile Val
              500            505            510

Val Ala Leu Arg Arg Arg His Thr Phe Lys Gly Asp Tyr Ser Thr
          515            520            525

Lys Lys His Val Tyr Gly Asn Gly Tyr Ser Lys Ala Gly Ile Pro Gln
          530            535            540

His His Pro Pro Met Ala Gln Asn Leu Gln Tyr Pro Asp Asp Ser Asp
545            550            555            560

Asp Glu Lys Lys Ala Gly Pro Leu Gly Gly Ser Ser Tyr Glu Glu Glu
              565            570            575

Glu Glu Glu Glu Glu Gly Gly Gly Gly Gly Glu Arg Lys Val Gly Gly
              580            585            590

Pro His Pro Lys Tyr Asp Glu Asp Ala Lys Arg Pro Tyr Phe Thr Val
              595            600            605

Asp Glu Ala Glu Ala Arg Gln Asp Gly Tyr Gly Asp Arg Thr Leu Gly
          610            615            620

Tyr Gln Tyr Asp Pro Glu Gln Leu Asp Leu Ala Glu Asn Met Val Ser
625            630            635            640

Gln Asn Asp Gly Ser Phe Ile Ser Lys Lys Glu Trp Tyr Val
              645            650
```

<210> SEQ ID NO 8

-continued

```
<211> LENGTH: 70
<212> TYPE: DNA
<213> ORGANISM: Artificial sequence
<220> FEATURE:
<223> OTHER INFORMATION: Primer gH5_galK_r

<400> SEQUENCE: 8
tcgtgggggt tattattttg ggcgttgcgt ggggtcaggt ccacgactgg tcagcactgt      60
cctgctcctt                                                             70

<210> SEQ ID NO 9
<211> LENGTH: 74
<212> TYPE: DNA
<213> ORGANISM: Artificial sequence
<220> FEATURE:
<223> OTHER INFORMATION: Primer gH6_galK_f

<400> SEQUENCE: 9
atgcggtcca tgcccaggcc atccaaaaac catgggtctg tctgctcagt cctgttgaca      60
attaatcatc ggca                                                        74

<210> SEQ ID NO 10
<211> LENGTH: 27
<212> TYPE: DNA
<213> ORGANISM: Artificial sequence
<220> FEATURE:
<223> OTHER INFORMATION: Primer galK_129_f

<400> SEQUENCE: 10
acaatctctg tttgccaacg catttgg                                          27

<210> SEQ ID NO 11
<211> LENGTH: 27
<212> TYPE: DNA
<213> ORGANISM: Artificial sequence
<220> FEATURE:
<223> OTHER INFORMATION: Primer galK_417_r

<400> SEQUENCE: 11
cattgccgct gatcaccatg tccacgc                                          27

<210> SEQ ID NO 12
<211> LENGTH: 60
<212> TYPE: DNA
<213> ORGANISM: Artificial sequence
<220> FEATURE:
<223> OTHER INFORMATION: GCN4 peptide cassette - nucleotide sequence of
      GCN4 peptide, bracketed by upstream and downstream GS linkers

<400> SEQUENCE: 12
ggatccaaga actaccacct ggagaacgag gtggccagac tgaagaagct ggtgggcagc      60

<210> SEQ ID NO 13
<211> LENGTH: 20
<212> TYPE: PRT
<213> ORGANISM: Artificial sequence
<220> FEATURE:
<223> OTHER INFORMATION: GCN4 peptide

<400> SEQUENCE: 13

Gly Ser Lys Asn Tyr His Leu Glu Asn Glu Val Ala Arg Leu Lys Lys
1               5                   10                  15

Leu Val Gly Ser
            20
```

-continued

```
<210> SEQ ID NO 14
<211> LENGTH: 12
<212> TYPE: PRT
<213> ORGANISM: Artificial sequence
<220> FEATURE:
<223> OTHER INFORMATION: GCN4 epitope

<400> SEQUENCE: 14

Tyr His Leu Glu Asn Glu Val Ala Arg Leu Lys Lys
1               5                   10

<210> SEQ ID NO 15
<211> LENGTH: 110
<212> TYPE: DNA
<213> ORGANISM: Artificial sequence
<220> FEATURE:
<223> OTHER INFORMATION: Oligonucleotide GCN4gH_23_42_fB

<400> SEQUENCE: 15
tcgtgggggt tattattttg ggcgttgcgt ggggtcaggt ccacgactgg ggatccaaga      60
actaccacct ggagaacgag gtggccagac tgaagaagct ggtgggcagc                 110

<210> SEQ ID NO 16
<211> LENGTH: 110
<212> TYPE: DNA
<213> ORGANISM: Artificial sequence
<220> FEATURE:
<223> OTHER INFORMATION: Oligonucleotide GCN4gH_23_24_rB

<400> SEQUENCE: 16
atgcggtcca tgcccaggcc atccaaaaac catgggtctg tctgctcagt gctgcccacc      60
agcttcttca gtctggccac ctcgttctcc aggtggtagt tcttggatcc                 110

<210> SEQ ID NO 17
<211> LENGTH: 27
<212> TYPE: DNA
<213> ORGANISM: Artificial sequence
<220> FEATURE:
<223> OTHER INFORMATION: Primer gH_ext_r pallino

<400> SEQUENCE: 17
gtttcttcct tttccccacc ccacccc                                          27

<210> SEQ ID NO 18
<211> LENGTH: 25
<212> TYPE: DNA
<213> ORGANISM: Artificial sequence
<220> FEATURE:
<223> OTHER INFORMATION: Primer gH_2176_2200_f

<400> SEQUENCE: 18
caggtaggtc ttcgggatgt aaagc                                            25

<210> SEQ ID NO 19
<211> LENGTH: 846
<212> TYPE: DNA
<213> ORGANISM: Saccharomyces cerevisiae

<400> SEQUENCE: 19
atgtccgaat atcagccaag tttatttgct ttaaatccaa tgggtttctc accattggat      60
ggttctaaat caaccaacga aaatgtatct gcttccactt ctactgccaa accaatggtt     120
ggccaattga tttttgataa attcatcaag actgaagagg atccaattat caaacaggat     180
```

-continued

```
acccccttcga  accttgattt  tgattttgct  cttccacaaa  cggcaactgc  acctgatgcc      240
aagaccgttt   tgccaattcc  ggagctagat  gccgctgtag  tggaatcttt  cttttcgtca      300
agcactgatt   caactccaat  gtttgagtat  gaaaacctag  aagacaactc  taaagaatgg      360
acatccttgt   ttgacaatga  cattccagtt  accactgacg  atgtttcatt  ggctgataag      420
gcaattgaat   ccactgaaga  agtttctctg  gtaccatcca  atctggaagt  ctcgacaact      480
tcattcttac   ccactcctgt  tctagaagat  gctaaactga  ctcaaacaag  aaaggttaag      540
aaaccaaatt   cagtcgttaa  gaagtcacat  catgttggaa  aggatgacga  atcgagactg      600
gatcatctag   gtgttgttgc  ttacaaccgc  aaacagcgtt  cgattccact  ttctccaatt      660
gtgcccgaat   ccagtgatcc  tgctgctcta  aaacgtgcta  gaaacactga  agccgccagg      720
cgttctcgtg   cgagaaagtt  gcaaagaatg  aaacaacttg  aagacaaggt  tgaagaattg      780
ctttcgaaaa   attatcactt  ggaaaatgag  gttgccagat  aaagaaatt   agttggcgaa      840 cgctga                                                                       846
```

```
<210> SEQ ID NO 20
<211> LENGTH: 281
<212> TYPE: PRT
<213> ORGANISM: Saccharomyces cerevisiae

<400> SEQUENCE: 20

Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
    50                  55                  60

Leu Asp Phe Asp Phe Ala Leu Pro Gln Thr Ala Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
            115                 120                 125

Pro Val Thr Thr Asp Asp Val Ser Leu Ala Asp Lys Ala Ile Glu Ser
        130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
            195                 200                 205

Asn Arg Lys Gln Arg Ser Ile Pro Leu Ser Pro Ile Val Pro Glu Ser
        210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255
```

-continued

```
Val Glu Glu Leu Leu Ser Lys Asn Tyr His Leu Glu Asn Glu Val Ala
            260                 265                 270

Arg Leu Lys Lys Leu Val Gly Glu Arg
        275                 280
```

HERPESVIRUS WITH MODIFIED GLYCOPROTEIN H FOR PROPAGATION IN A CELL

CROSS-REFERENCE TO RELATED APPLICATIONS

This application is the U.S. national phase application, pursuant to 35 U.S.C. § 371, of PCT International Application Ser. No.: PCT/EP2017/063949, filed Jun. 8, 2017, designating the United States and published in English, which claims priority to and the benefit of European Patent Application No. 16173831.5, filed Jun. 9, 2016. The entire contents of the aforementioned patent applications are incorporated herein by this reference.

BACKGROUND OF THE INVENTION

The work leading to this invention has received funding from the European Research Council under the European Union's Seventh Framework Program (FP7/2007-2013)/ ERC grant agreement no 340060.

Despite a steady development in healthcare, the burden of diseases and pathologies that cannot be treated or cannot be sufficiently treated, remains elevated. Eminent among these are numerous forms of tumors, in particular metastatic forms of tumors that are treated with chemo-radio-therapy or biological medicaments, or combinations thereof, however, with limited success.

An alternative approach of tumor treatment is oncolytic virotherapy, whereby a replication competent virus infects the tumor cells, spreads from cell to cell of the tumor and destroys them.

Herpes simplex virus (HSV) is a pathogen virus for humans. In culture, it infects a large number of mammalian cells. It is an enveloped virus which enters the cell by membrane fusion, either at the plasma membrane or through endocytosis, depending on the target cell type. Entry of HSV into a target cell is a multistep process, requiring complex interactions and conformational changes of viral glycoproteins gD, gH/gL, gC and gB. These glycoproteins constitute the virus envelope which is the most external structure of the HSV particle and consists of a membrane. For cell entry, gC and gB mediate the first attachment of the HSV particle to cell surface heparan sulphate. Thereafter, gD binds to at least two alternative cellular receptors, being Nectin-1 and HVEM or HVEA, causing conformational changes in gD that initiates a cascade of events leading to virion-cell membrane fusion. Thereby, the intermediate protein gH/gL (a heterodimer) is activated which triggers gB to catalyze membrane fusion. Thereby, gB is membrane bound and functions as a viral fusogen.

Oncolytic HSVs (o-HSV) have been used in recent years as oncolytic agents. As wild-type HSV viruses are highly virulent, there is a requirement that the o-HSVs are attenuated. T-VEC/Imlygic and the viruses that have reached clinical trials carry deletion of one or more HSV genes, including the gamma $\gamma_1 34.5$ gene, which encodes the ICP34.5 protein whose role is to preclude the shut off of protein synthesis in infected cells, and the UL39 gene, which encodes the large subunit of ribonucleotide reductase. In addition to some disadvantages which are shown by these viruses, such as the failure to produce high yield of progeny viruses, they furthermore have the preserved ability to bind to any cell bearing their natural receptors. Thus, the therapeutic effect of tumor cell killing is diminished and the viruses may have limitations in medical use.

One approach to overcome these limits has been genetic engineering of o-HSVs which exhibit a highly specific tropism for the tumor cells, and are otherwise not attenuated. This approach has been defined as retargeting of HSV tropism to tumor-specific receptors.

The retargeting of HSV to cancer-specific receptors entails the genetic modifications of gD, such that it harbors heterologous sequences which encode a specific ligand. Upon infection with the recombinant virus, progeny viruses are formed which carry in their envelope the chimeric gD-ligand glycoprotein, in place of wildtype gD. The ligand interacts with a molecule specifically expressed on the selected cell and enables entry of the recombinant o-HSV into the selected cell. Examples of ligands that have been successfully used for retargeting of HSV are IL13α, uPaR, a single chain antibody to HER2 and a single chain antibody to EGFR.

The retargeting through modification of glycoproteins has also been attempted with gC. The inserted ligands were EPO and IL13. The virus carrying the gC-EPO polypeptide attached to cells expressing the EPO receptor. However, this attachment did not lead to infectious entry. In addition, the gC-IL13 polypeptide was present in a virus that carried a second copy of IL13 in the gD gene. Therefore, it cannot be inferred from those studies whether the gC-IL13 contributed or not to the retargeting to the IL13 alpha2 receptor.

The retargeting through genetic modification of gH has also been achieved. The inserted ligand was a single-chain antibody (scFv) directed to HER2, without or with deletions within the gH gene. The virus was successfully retargeted to a cell carrying the HER2 receptor (Gatta et al., 2015). In addition, a recombinant virus was constructed which contained the scFv directed to HER2 in gH and an scFv directed to EGFR in the mature gD protein. This resulted in double retargeting to the cells carrying the receptors. Further, a recombinant virus was constructed which contained the scFv directed to HER2 in gH and the scFv directed to HER2 in the mature gD protein. This resulted in double retargeting to the HER2 receptors (Abstract No. P-28, 9th International conference on Oncolytic virus Therapeutics, Boston 2015).

While the art knows methods for retargeting of HSV to disease-specific receptors, these HSVs with the capability of being retargeted need to be propagated so that they can be produced in high amounts and are available as pharmaceuticals for treating diseases. In view of the fact that, for reasons of safety, the cells for propagation and production of the HSVs should not be diseased cells, so as to avoid the introduction of material such as DNA, RNA and/or protein of the diseased cells such as tumor cells in humans, the HSVs need to comprise additional modifications for enabling the HSVs of infecting "safe" cells which do not produce components which are harmful to humans for propagation and production of the HSVs. However, the prior art has not disclosed so far methods which enable the propagation and production of herpesviruses with the capability of being retargeted to disease-specific receptors in safe cells.

Thus, there is a need in the art to provide retargeting strategies for retargeting herpesvirus with the capability of being retargeted to disease-specific receptors and to cells which can be safely used for the propagation and production of the herpesvirus.

The present invention describes a recombinant HSV with a modified gH protein which retargets the herpesvirus to receptors of cells which are able to safely propagate and produce the herpesvirus.

The present inventors have shown that it is possible to construct a recombinant HSV which comprises a part of the GCN4 yeast transcription factor as a fusion protein with gH, whereby due to the presence of the part of the GCN4 yeast transcription factor, the HSV is retargeted to cells carrying a receptor of the part of the GCN4 yeast transcription factor. Furthermore, the HSV has been shown to maintain infectivity, resulting in the entry into the cells carrying the receptor and propagation and production of the HSV.

DETAILED DESCRIPTION OF THE INVENTION

In the following, the present invention is described in detail. The features of the present invention are described in individual paragraphs. This, however, does not mean that a feature described in a paragraph stands isolated from a feature or features described in other paragraphs. Rather, a feature described in a paragraph can be combined with a feature or features described in other paragraphs.

The term "comprise/es/ing", as used herein, is meant to "include or encompass" the disclosed features and further features which are not specifically mentioned. The term "comprise/es/ing" is also meant in the sense of "consist/s/ing of" the indicated features, thus not including further features except the indicated features. Thus, the product of the present invention may be characterized by additional features in addition to the features as indicated.

In a first aspect, the present invention provides a recombinant herpesvirus comprising a peptide having a length of 5 to 274 amino acids, fused to or inserted into glycoprotein H (gH) present in the envelope of the herpesvirus.

In an embodiment thereof, the peptide has a length of 5 to 200 amino acids, preferably of 11 to 29, 31 to 39, 41 to 49 or 51 to 200 amino acids, more preferably of 12 to 20 amino acids.

In an embodiment thereof, the peptide comprises a part of the GCN4 yeast transcription factor, preferably the part of the GCN4 yeast transcription factor as comprised by SEQ ID NO: 13, most preferably the peptide is the peptide identified by SEQ ID NO: 13.

In an embodiment thereof, the peptide is inserted within the N-terminal region starting at any one of amino acids 19 to 23 and ending at any one of amino acids 48 to 88 or starting at amino acid 116 and ending at amino acid 136 of the gH according to SEQ ID NO: 1 or a corresponding region of a homologous gH.

In an embodiment thereof, the peptide is inserted N-terminally of the H1A domain of gH.

In an embodiment thereof, one or more gH amino acids of the N-terminal region are deleted.

In an embodiment thereof, the herpesvirus has the capability of binding to a cell expressing or binding a target molecule via the peptide, preferably of fusing with the cell membrane, more preferably of entering the cell, most preferably of propagating within the cell.

In an embodiment thereof, the target molecule is the scFv as comprised by SEQ ID NO: 5, most preferably the molecule identified by the sequence of SEQ ID NO: 7.

In an embodiment thereof, the herpesvirus comprises a gD which is modified to retarget the herpesvirus to a diseased cell and/or a gB which is modified to retarget the herpesvirus to a diseased cell.

In an embodiment thereof, the herpesvirus encodes one or more molecule(s) that stimulate(s) the host immune response against a cell, preferably a diseased cell. The recombinant herpesvirus of the present invention serves the purpose of infecting and killing diseased cells in humans. This requires the provision of the herpesvirus and, therefore, its propagation and production. As propagation of the herpesvirus shall be avoided in diseased cells, so as to avoid the introduction of material such as DNA, RNA and/or protein of the diseased cells such as tumor cells into humans, the recombinant herpesvirus has to be engineered to be capable of infecting cells which are useful for the production of the herpesvirus and do not produce material which may be harmful to humans. Such cells are also referred to herein as "safe" cells. This requires the retargeting of the recombinant herpesvirus of the present invention to such cells for propagation and production. To achieve this, glycoprotein H of the recombinant herpesvirus is modified to include a peptide, namely a peptide of 5 to 274 amino acids, preferably of 5 to 200 amino acids, more preferably of 11 to 29, 31 to 39, 41 to 49 or 51 to 200 amino acids, such as 11, 12, 13, 14, 15, 16, 17, 18, 19, 20, 21, 22, 23, 24, 25, 26, 27, 28, or 29 amino acids, still more preferably of 12 to 20 amino acids, still more preferably a part of the GCN4 yeast transcription factor, still more preferably the part of the GCN4 yeast transcription factor as comprised by SEQ ID NO: 13, most preferably the peptide identified by SEQ ID NO: 13, which allows for binding to a target molecule which is accessible on the surface of a cell which can be safely used for the production of the herpesvirus. The use of the peptide as a ligand for binding to a target molecule requires the accessibility of such target molecule on a cell which can be safely used for propagating and producing the recombinant herpesvirus. This in turn requires the modification of cells which are capable of safely producing the recombinant herpesvirus of the present invention to comprise target molecules capable of binding to the peptide. Preferred target molecules are antibodies or antibody derivatives such as scFvs such as the scFv as comprised by SEQ ID NO: 5, which are specifically generated as target molecules to fit to the ligand.

The recombinant herpesvirus of the present invention may additionally comprise heterologous polypeptide ligand(s) in other glycoprotein(s) such as gD and/or gB involved in herpesvirus entry into a cell for retargeting the herpesvirus to target molecules present in unwanted such as diseased cells. Thus, while the modification of gH serves the purpose of retargeting the herpesvirus to a cell for production, further modifications of other glycoproteins serve the purpose of retargeting the herpesvirus to target molecules on unwanted cells for killing them.

Glycoprotein H (gH) is a 110 kDa virion envelope glycoprotein that plays a role in herpesvirus infectivity. It forms a heterodimer with herpesvirus glycoprotein L. Upon entry of herpesvirus into a cell, the heterodimer gH/gL interacts with the profusion domain of glycoprotein D (gD) which profusion domain is dislodged upon interaction of gD with one of its receptors, Nectin-1, HVEM, and modified heparan sulfates during cell entry. When a herpesvirus does not comprise a gD molecule, gH/gL interacts with analogous proteins having the same function as gD such as gp42 encoded by Epstein Barr virus. This interaction is the critical event in the activation cascade of the four glycoproteins gD, gH, gL, and gB, which are involved in herpesvirus entry into a cell. The activation cascade starts with the binding of gD to one of its receptors and results in the fusion of the herpesvirus with the target cell membrane mediated by gB. Among at least human and monkey herpesviruses, gH is conserved. Crystal structures of the extracellular portion of three gH proteins are known: one from the alphaherpesvirus HSV-2 gH (Chowdary et al., 2010), one from the swine PrV (Backovic et al., 2012), also an alphaherpesvirus, and one from Epstein-Barr virus (Matsuura et al., 2010), a gamma herpesvirus. They are substantially similar, for example, an organization in structurally similar domains is present in all crystal structures. The nucleotide and amino acid sequences of a variety of gHs of different herpesviruses are known in the art. For illustrative purposes only, without being limited thereto, reference is made to the amino acid sequence of gH of human herpesvirus 1 disclosed herein as SEQ ID NO: 1. The corresponding nucleotide sequence and the amino acid sequence are available from the NCBI (National Centre for Biotechnology Information; National Library of Medicine, Bethesda, MD 20894, USA; www.ncbi.nlm.nih.gov) under the accession number "Genome", GU734771.1, coordinates from 43741 to 46498.

6 identical in corresponding positions in two optimally aligned sequences. It is determined by comparing two optimally aligned sequences over a comparison window, where the fragment of the amino acid sequence in the comparison window may comprise additions or deletions (e.g., gaps or overhangs) as compared to the reference sequence, SEQ ID NO: 1 (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local

```
                                             SEQ ID NO: 1
   1  MGNGLWFVGV  IILGVAWGQV  HDWTEQTDPW  FLDGLGMDRM  YWRDTNTGRL  WLPNTPDPQK

61  PPRGFLAPPD  ELNLTTASLP  LLRWYEERFC  FVLVTTAEFP  RDPGQLLYIP  KTYLLGRPPN

121  ASLPAPTTVE  PTAQPPPSVA  PLKGLLYNPV  ASVLLRSRAW  VTFSAVPDPE  ALTFPRGDNV

181  ATASHPSGPR  DTPPPRPPVG  ARRHPTTELD  ITHLHNASTT  WLATRGLLRS  PGRYVYFSPS

241  ASTWPVGIWT  TGELVLGCDA  ALVRARYGRE  FMGLVISMHD  SPPVEVMVVP  AGQTLDRVGD

301  PADENPPGAL  PGPPGGPRYR  VFVLGSLTRA  DNGSALDALR  RVGGYPEEGT  NYAQFLSRAY

361  AEFFSGDAGA  EQGPRPPLFW  RLTGLLATSG  FAFVNAAHAN  GAVCLSDLLG  FLAHSRALAG

421  LAARGAAGCA  ADSVFFNVSV  LDPTARLQLE  ARLQHLVAEI  LEREQSLALH  ALGYQLAFVL

481  DSPSAYDAVA  PSAAHLIDAL  YAEFLGGRVL  TTPVVHRALF  YASAVLRQPF  LAGVPSAVQR

541  ERARRSLLIA  SALCTSDVAA  ATNADLRTAL  ARADHQKTLF  WLPDHFSPCA  ASLRFDLDES

601  VFILDALAQA  TRSETPVEVL  AQQTHGLAST  LTRWAHYNAL  IRAFVPEASH  RCGGQSANVE

661  PRILVPITHN  ASYVVTHSPL  PRGIGYKLTG  VDVRRPLFLT  YLTATCEGST  RDIESKRLVR

721  TQNQRDLGLV  GAVFMRYTPA  GEVMSVLLVD  TDNTQQQIAA  GPTEGAPSVF  SSDVPSTALL

781  LFPNGTVIHL  LAFDTQPVAA  IAPGFLAASA  LGVVMITAAL  AGILKVLRTS  VPFFWRRE*
```

40 gH homologs are found in all members of the Herpesviridae. Therefore, the term "glycoprotein H", as referred to herein, refers to any gH homolog found in Herpesviridae. Alternatively, gH, as referred to herein, refers to any gH which has an amino acid identity to the sequence of SEQ ID NO: 1 of at least 70%, 80%, 85%, 90%, 95%, 96%, 97%, 98%, 99% or 100%. Alternatively, the gH, as referred to herein, refers to any gH which has an amino acid homology to SEQ ID NO: 1 of at least 50%, 60%, 70%, 80%, 85%, 90%, 95%, or 100%. The gH, as referred to herein, also includes a fragment of gH. Preferably, gH, as referred to herein, including any gH found in Herpesviridae, any gH having an amino acid identity to the sequence of SEQ ID NO: 1, as defined above, and any fragment of a gH, has the same activity of the gH according to SEQ ID NO: 1. More preferably, a gH homolog plays a critical role in herpesvirus entry into a cell. Namely, during the entry process of the virus into a cell, the heterodimer gH/gL interacts with the profusion domain of gD, or analogous proteins, e.g. gp42 encoded by Epstein Barr virus, or with cellular receptors to gH/gL, including but not limited to integrins. These events lead to an activation cascade of the four glycoproteins gD or an analogous protein, gH, gL, and gB, involved in herpesvirus entry.

The percentage of "sequence identity," as used herein, refers to the percentage of amino acid residues which are homology algorithm of Smith and Waterman, 1981, by the homology alignment algorithm of Needleman and Wunsch, 1970, by the search for similarity method of Pearson and Lipman, 1988, by the algorithm of Karlin and Altschul, 1990, modified by Karlin and Altschul, 1993, or by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by inspection. GAP and BESTFIT are preferably employed to determine the optimal alignment. Typically, the default values of 5.00 for gap weight and 0.30 for gap weight length are used.

The "percentage of homology", as used herein, refers to the percentage of amino acid residues which are homologous in corresponding positions in two optimally aligned sequences. The "percentage of homology" between two sequences is established in a manner substantially identical to what has been described above with reference to the determination of the "percentage of identity" except for the fact that in the calculation also homologous positions and not only identical positions are considered. Two homologous amino acids have two identical or homologous amino acids. Homologous amino acid residues have similar chemical-physical properties, for example, amino acids belonging to a same group: aromatic (Phe, Trp, Tyr), acid (Glu, Asp), polar (Gln, Asn), basic (Lys, Arg, His), aliphatic (Ala, Leu, lie, Val), with a hydroxyl group (Ser, Thr), or with a short lateral chain (Gly, Ala, Ser, Thr, Met). It is expected that substitutions between such homologous amino acids do not change a protein phenotype (conservative substitutions).

A gH is "homologous" or a "homolog" if it has an identity to SEQ ID NO: 1 of at least 70%, 80%, 85%, 90%, 95%, 96%, 97%, 98%, 99%, or 100%, if it has an amino acid homology to SEQ ID NO: 1 of at least 50%, 60%, 70%, 80%, 85%, 90%, 95%, or 100%, or if it has the same activity as the gH according to SEQ ID NO: 1. Preferably, "same activity" may be understood in the sense that the heterodimer gH/gL interacts with the profusion domain of gD or an analogous protein, thus playing a critical role in the activation cascade of the four glycoproteins gD or an analogous protein, gH, gL, and gB, involved in herpesvirus entry. A homolog may also be a fragment of a full length gH having the activity as indicated above.

The chimeric gH of the present invention (as exemplified by SEQ ID NO: 3) carries the peptide and thereby confers a new activity on the virus, in addition to the activity that the gH portion carries out for the wildtype (wt) virus. The chimeric gH, once it is part of the envelope of the recombinant virus, enables the binding of the recombinant virus to a target molecule, which can be bound by the peptide, and retargets the tropism of recombinant virus to a cell carrying the target molecule. Preferably, the heterodimer gH/gL interacts with the profusion domain of gD or an analogous protein, which is a critical event in the activation cascade of the four glycoproteins gD or an analogous protein, gH, gL, and gB, involved in herpesvirus entry. After fusion with a cell carrying the target molecule of the peptide, the recombinant herpesvirus enters the cell, and the cell infected by the recombinant herpesvirus produces proteins encoded by the viral genome, including the chimeric gH harboring the peptide. The infected cell produces progeny virus which is released from the cell by lysis of the cell. The herpesvirus thus produced can be isolated and used for intended purposes, e.g. as a pharmaceutical.

The indication of a specific amino acid number or region of gH, as used herein, refers to the "precursor" form of gH, as exemplified in SEQ ID NO: 1 that includes the N-terminal signal sequence comprising the first 18 amino acids. The "mature" form of gH starts with amino acid 19 of SEQ ID NO: 1 and extends until amino acid 838. As gH glycoproteins with amino acid sequences different from SEQ ID NO: 1 are also comprised by the present invention, the indication of a specific amino acid number or of a specific amino acid region which relates to SEQ ID NO: 1 means also the amino acid number or region of a homologous gH, which corresponds to the respective amino acid number or region of SEQ ID NO: 1.

The term "chimeric glycoprotein H" or "chimeric gH", as used herein, means a gH having fused to or inserted into the gH the peptide. The chimeric gH is encoded by the recombinant virus, is synthesized with the cell that produces the recombinant virus, and becomes incorporated in the envelope of the virion. Methods to produce the recombinant viruses by genetic engineering are known in the art. Methods for producing chimeric glycoprotein H are known in the art.

The term "retargeting", as used herein, means that the recombinant herpesvirus of the present invention is targeted to the target molecule which is bound by the ligands introduced into the herpesvirus. However, the recombinant herpesvirus is still capable of being targeted to the natural receptor of the unmodified herpesvirus. Retargeting is different form "detargeting", which means that the recombinant herpesvirus is no longer capable of being targeted to the natural receptor of the unmodified herpesvirus. "Detargeting" means that the recombinant virus is only targeted to the target molecule of the ligand.

The GCN4 yeast transcription factor is state of the art (see e.g. Arndt and Fin, 1986; Hope and Struhl, 1987). An exemplary GCN4 yeast transcription factor is one identified by SEQ ID NO: 20 (UniProtKB—P03069) encoded by the gene identified in SEQ ID NO: 19 (GenBank accession No. AJ585687.1). The term "GCN4 yeast transcription factor", as referred to herein, refers to any GCN4 yeast transcription factor present in nature. Alternatively, GCN4 yeast transcription factor, as referred to herein, refers to any GCN4 yeast transcription factor which has an amino acid identity to the sequence of SEQ ID NO: 20 of at least 70%, 80%, 85%, 90%, 95%, 96%, 97%, 98%, 99% or 100%. Alternatively, the GCN4 yeast transcription factor, as referred to herein, refers to any GCN4 yeast transcription factor which has an amino acid homology to SEQ ID NO: 20 of at least 50%, 60%, 70%, 80%, 85%, 90%, 95%, or 100%. A GCN4 yeast transcription factor is "homologous" or a "homolog" if it has an identity to SEQ ID NO: 1 of at least 70%, 80%, 85%, 90%, 95%, 96%, 97%, 98%, 99%, or 100%, if it has an amino acid homology to SEQ ID NO: 1 of at least 50%, 60%, 70%, 80%, 85%, 90%, 95%, or 100%, or if it has the same activity as the GCN4 yeast transcription factor according to SEQ ID NO: 20. Preferably, "same activity" may be understood in the sense that GCN4 yeast transcription factor works as a transcription factor in the same way as the GCN4 yeast transcription factor according to SEQ ID NO: 20. The term "a part thereof", as used herein, comprises any part of the GCN4 yeast transcription factor against which a target molecule can be generated to which the "part thereof" is capable of binding. Preferably, the length of "the part thereof" is such that a peptide length of 5 to 274 amino acids, preferably 5 to 200 amino acids, more preferably 11 to 29, 31 to 39, 41 to 49 or 51 to 200 amino acids, such as 11, 12, 13, 14, 15, 16, 17, 18, 19, 20, 21, 22, 23, 24, 25, 26, 27, 28, or 29 amino acids, still more preferably 12 to 20 amino acids results, whereby the peptide may include additional amino acids such as linker sequences. Most preferably, the length of the "the part thereof" is 12 amino acids. The most preferred "part thereof" is the epitope YHLENEVARLKK (SEQ ID NO: 14) of GCN4 yeast transcription factor. For fusion to or insertion into gH, the epitope YHLENE-VARLKK may further comprise two flanking wt (wildtype) GCN4 residues on each side and two GS linkers. This construct is herein named GCN4 peptide. This 20 amino acid peptide confers to the herpesvirus the ability to infect and replicate in a cell line bearing a target molecule to which the "part thereof" binds.

The present invention discloses a recombinant herpesvirus comprising the GCN4 yeast transcription factor, fused to or inserted into glycoprotein H (gH) present in the envelope of the herpesvirus.

The term "recombinant" herpesvirus, as referred to herein, refers to a herpesvirus that has been genetically engineered by genetic recombination to include additional nucleic acid sequences which encode the peptide. Methods of producing recombinant herpesviruses are well known in the art (see for example Sandri-Goldin et al., 2006). However, the present invention is not limited to genetic engineering methods. Also other methods may be used for producing a herpesvirus having fused or inserted a peptide to or into gH, respectively.

The term "herpesvirus", as referred to herein, refers to a member of the Herpesviridae family of double-stranded DNA viruses, which cause latent or lytic infections. Herpesviruses all share a common structure in that their genomes consist of relatively large (about from 100.000 to 200.000 base pairs), double-stranded, linear DNA encoding 80 to 200 genes, encased within an icosahedral protein cage called the capsid which is itself wrapped by a protein layer called the tegument containing both viral proteins and viral mRNAs and a lipid bilayer membrane called the envelope. This whole particle is also known as a virion. The term "herpesvirus" also refers to members of the Herpesviridae family which are mutated comprising one or more mutated genes, such as, e.g., herpesviruses which were modified in a laboratory.

In a preferred embodiment, the herpesvirus is selected from the group consisting of Herpes Simplex Virus 1 (HSV-1), Herpes Simplex Virus 2 (HSV-2), Varicella Zoster Virus (human herpesvirus 3 (HHV-3)), swine alphaherpesvirus Pseudorabievirus (PRV), chimpanzee alpha1 herpesvirus (ChHV), Papiine herpesvirus 2 (HVP2), Cercopithecine herpesvirus 2 (CeHV2), Macacine herpesvirus 1 (MHV1), Saimiriine herpesvirus 1 (HVS1), Callitrichine herpesvirus 3 (CalHV3), Saimiriine herpesvirus 2 (HVS2), Bovine herpesvirus 1 (BoHV-1), Bovine Herpesvirus 5 (BoHV-5), Equine herpesvirus 1 (EHV-1), Equine herpesvirus 2 (EHV-2), Equine herpesvirus 5 (EHV-5), Canine herpesvirus 1 (CHV), Feline herpesvirus 1 (FHV-1), Duck enteritis virus (DEV), Fruit bat alphaherpesvirus 1 (FBAHV1), Bovine herpesvirus 2 (BoHV-2), Leporid herpesvirus 4 (LHV-4), Equine herpesvirus 3 (EHV-3), Equine herpesvirus 4 (EHV-4), Equine herpesvirus 8 (EHV-8), Equid herpesvirus 9 (EHV-9), Cercopithecine herpesvirus 9 (CeHV-9), Suid herpesvirus 1 (SuHV-1), Marek's disease virus (MDV), Marek's disease virus serotype 2 (MDV2), Falconid herpesvirus type 1 (FaHV-1), Gallid herpesvirus 3 (GaHV-3), Gallid herpesvirus 2 (GaHV-2), Lung-eye-trachea disease-associated herpesvirus (LETV), Gallid herpesvirus 1 (GaHV-1), Psittacid herpesvirus 1 (PsHV-1), Human herpesvirus 8 (HHV-8), Human herpesvirus 4 (HHV-4), Chelonid herpesvirus 5 (ChHV5), Ateline herpesvirus 3 (AtHV3) or Meleagrid herpesvirus 1 (MeHV-1). In a more preferred embodiment, the herpesvirus is HSV-1 or HSV-2, most preferably HSV-1.

The term "peptide", as used herein, is a continuous and unbranched peptide chain consisting of amino acids connected by peptide bonds. The length of the peptide chain is 5 to 274 amino acids, preferably 5 to 200 amino acids, more preferably 11 to 29, 31 to 39, 41 to 49 or 51 to 200 amino acids, still more preferably 12 to 20 amino acids, still more preferably the peptide comprises a part of the GCN4 yeast transcription factor, still more preferably the part of the GCN4 yeast transcription factor as comprised by SEQ ID NO: 13, most preferably the peptide is the peptide identified by SEQ ID NO: 13. In the present invention, the peptide is used as a fusion to or insertion into gH. The peptide, if not specifically defined, may be any peptide to which a target molecule which is present on a target cell is capable of binding. Thus, the peptide may be a part of a natural polypeptide. The natural polypeptide may be derived from any organism, preferably from an organism which is not harmful to human. For example, the natural polypeptide is a fungal or bacterial polypeptide, such as a polypeptide from the genus *Saccharomyces* such as *Saccharomyces cerevisiae*. As the peptide is capable of binding to a target molecule present on a cell, the peptide represents a ligand. The term "ligand" is generally used herein as binding to or being capable of binding to a target molecule accessible on the surface of a cell.

The term "polypeptide", as used herein, is a continuous and unbranched peptide chain consisting of amino acids connected by peptide bonds. The length of the polypeptide chain is unlimited and may range from some amino acids such as 5 amino acids to some hundreds or thousands amino acids. More than one polypeptide chains may assemble to a complex such as an antibody. The term "polypeptide", as used herein, also comprises an assembly of polypeptide chains. While the term "peptide" is used herein for a ligand which is inserted into or fused to gH, the term "polypeptide" is used herein for ligands inserted into gD or gB which serve to target diseased cells, for the gH polypeptide having fused to or inserted the peptide or for specific polypeptides as indicated.

The term "corresponding region of a homologous gH" refers to a region of a gH which aligns with a given region of the gH according to SEQ ID NO: 1 when using the Smith-Waterman algorithm and the following alignment parameters: MATRIX: BLOSUM62, GAP OPEN: 10, GAP EXTEND: 0.5. This algorithm is generally known and used in the art if performing pairwise sequence comparisons and the skilled person knows how to apply it. In case only a part or parts of the given region of SEQ ID NO: 1 aligns with the sequence of a homologous gH using above algorithm and parameters, the term "corresponding region" refers to the region which aligns with the part(s) of the given region of SEQ ID NO: 1. In this case, the region in the homologous gH, in which the peptide is inserted, comprises only the amino acids which align with the part(s) of the given region of SEQ ID NO: 1. The term "corresponding region" may also refer to a region which is flanked by corresponding flanking sequences, wherein the flanking sequences align, using above algorithm and parameters, with sequences flanking the region of SEQ ID NO: 1. These flanking sequences are at least 5, 6, 7, 8, 9, 10, 15, 20, 30, 40 or 50 amino acids long. Other algorithms which may be used are the algorithms of Needleman and Wunsch, 1970, the similarity method of Pearson and Lipman, 1988, or the algorithm of Karlin and Altschul, 1990, modified by Karlin and Altschul, 1993, or computerized implementations of these algorithms.

The term "corresponding amino acid" refers to an amino acid which is present within a corresponding region and which is the counterpart of a given amino acid of SEQ ID NO: 1 in the alignment. A corresponding amino acid must not be identical to its counterpart in SEQ ID NO: 1 in the alignment, as far as it is present within a corresponding region.

In the recombinant herpesvirus of the present invention, the peptide may be fused to or inserted into gH. In this context, the term "fused" or "fusion", as referred to herein, refers to the addition of the peptide to the N-terminal amino acid of gH by peptide bonds, either directly or indirectly via a peptide linker. "Fused" or "fusion" to the N-terminal region is different from "insertion" insofar as "fused" or "fusion" means addition to the terminus of gH, whereas "insertion" means incorporation into the gH.

A peptide linker, as referred to herein, serves to connect amino acid sequences derived from different sources. Such a linker serves to connect and to enable proper folding of the peptide with glycoprotein H sequences. It may also serve to connect peptide sequences with glycoprotein sequences other than gH. A linker has typically a length between 1 and 30 amino acids, preferably 2 to 25 amino acids, more preferably 2 to 10 amino acids, most preferably 2 amino acids and may comprise any amino acids. Preferably, it comprises the amino acid(s) Gly and/or Ser and/or Thr, more preferably it comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids selected from the group consisting of Gly, Ser and/or Thr. Still more preferably, it consists of the amino acids Gly and/or Ser. Linkers based on Gly and/or Ser provide flexibility, good solubility and resistance to proteolysis. Alternatively, the linker may not predominantly comprise glycine, serine and/or threonine, but glycine, serine and/or threonine may not be present or only to a minor extent. The most preferred linker to connect the peptide with gH sequences is the linker GS. In case of insertion, it is present on both sides of the peptide.

In the recombinant herpesvirus of the present invention, the peptide is fused to or inserted into the gH glycoprotein. Preferably, the peptide is inserted within the N-terminal region of gH starting at any one of amino acids 19 to 23 (preferably 19) and ending at any one of amino acids 48 to 88 (preferably 88), preferably starting at amino acid 19 and ending at amino acid 88, starting at amino acid 61 and ending at amino acid 65, starting at amino acid 69 and ending at amino acid 72, or starting at amino acid 74 and ending at amino acid 80; or is inserted within a region starting at amino acid 116 and ending at amino acid 136 of the gH according to SEQ ID NO: 1 or a corresponding region of a homologous gH. The ranges 61-65, 69-72 and 74-80 are thought to be particularly useful since they represent exposed loop regions of the gH H1A domain and therefore represent insertion points that retain the structural integrity of the gH H1A domain. In a more preferred embodiment, it is inserted within the N-terminal region of gH starting at amino acid 19 and ending at amino acid 50 of the gH according to SEQ ID NO: 1 or a corresponding region of a homologous gH. In an even more preferred embodiment, it is inserted within the N-terminal region of gH starting at amino acid 19 and ending at amino acid 48 of the gH according to SEQ ID NO: 1 or a corresponding region of a homologous gH. In another more preferred embodiment, it is inserted within the N-terminal region of gH starting at amino acid 23 and ending at amino acid 48 of the gH according to SEQ ID NO: 1 or a corresponding region of a homologous gH. In all these embodiments, the amino acids defining start and end of a region are included in the region, i.e. the insertion may by either N-terminal or C-terminal of the start or end amino acid. In the most preferred embodiment, the peptide is inserted between amino acid 23 and amino acid 24 of the gH according to SEQ ID NO: 1 or a corresponding region (in this case corresponding to said amino acids 23 and 24) of a homologous gH. In a particular embodiment, one or more gH amino acids of the N-terminal region as specified above are deleted. In a related embodiment, gH is truncated.

In another embodiment, the peptide is inserted N-terminally of the H1A domain of gH. N-terminally inserted in this respect does not mean adjacent to the H1A domain on the N-terminal side, but anywhere on the N-terminal side of the H1A domain. The H1A domain of gH is a subdomain of the HI domain of gH. The H1 domain extends from amino acid 49 to 327 of the gH protein according to SEQ ID NO: 1, and the H1A domain extends from amino acid 49 to 115 of the gH protein according to SEQ ID NO: 1 (Chowdary et al., 2010). Many gH proteins have a H1A domain, which can be identified by sequence alignment with SEQ ID NO: 1 or by structural similarity within the H1 domain as is the case for gH from Varicella Zoster Virus (human herpesvirus 3). Not every herpesvirus may have a gH with a region corresponding to amino acids 1 to 48 of the gH protein according to SEQ ID NO: 1. However, every mature gH has at least some, e.g. 1, 2 or 3 amino acids N-terminally of the H1A domain. An example is EBV, wherein only 1 residue precedes the H1A domain in the mature peptide (assuming that the H1A domain starts at the first residue visible in the X-ray structure, i.e. for EBV position 19 of the gH precursor). In case of a gH in which this preceding region is very short, for example 10 or less, 5 or less, or 3 or less amino acids, it is envisaged that the insertion is behind (i.e. C-terminally of) these residues and, that, optionally, these residues are duplicated behind the insertion, i.e. between the insertion and the H1A domain.

The term "inserted" or "insertion", as referred to herein in the sense that the peptide is inserted into gH, refers to the incorporation into the gH, wherein the incorporated peptide is introduced between two amino acids of the gH by peptide bonds, either directly or indirectly via one or more peptide linkers, more specifically via an upstream and/or downstream located peptide linker with respect to the insert. The linker is directly connected to the peptide. The fusion of the peptide to gH can also be seen as an insertion of the peptide sequence into the gH precursor, exemplified by SEQ ID NO: 1 or a homologous gH, directly before amino acid 1 of the gH; such an insertion is herein termed as fusion. The gH carrying the fused, or inserted peptide is herein referred to chimeric gH. The chimeric gH is part of the virion envelope. The definition of "linker" is, as described above.

The insertion and fusion are preferably carried out by genetic engineering of the gH gene, in the genome of HSV. The genetic engineering of HSV genomes is known in the art, exemplified by, but not limited to, BAC technologies The peptide which is present in the envelope of the recombinant herpesvirus of the present invention enables the recombinant herpesvirus to enter into any cell which expresses or binds a target molecule to which the peptide is capable of binding. Consequently, as used herein, the target molecule may be any molecule which is accessible on the surface of a cell and which can be bound by the peptide. Preferably, the target molecule is an artificial molecule which is not naturally produced by the target cell which is used for propagation and production of the recombinant herpesvirus. Thus, the term "artificial target molecule", as referred to herein, may be a natural molecule which is not naturally produced by the target cell such as an antibody or a molecule which does not naturally occur, i.e. that has a non-natural amino acid sequence such as an antibody derivative. Such artificial molecule may be constructed to be expressed by a cell on its surface, as e.g. described in Douglas et al., 1999; and Nakamura et al., 2005, or it may be bound by a cell surface. The artificial target molecule is specifically designed so that it can be bound by the peptide. Examples of artificial target molecules bound by the peptide are antibodies or antibody derivatives. Preferred artificial target molecules are scFvs, more preferably an scFv capable of binding to a part of the GCN4 yeast transcription factor, still more preferably an scFv capable of binding to the part of the GCN4 yeast transcription factor as comprised by SEQ ID NO: 13, still more preferably the scFv as comprised by SEQ ID NO: 5 (Zahnd et al., 2004), most preferably the molecule identified by the sequence of SEQ ID NO: 7. Methods for producing antibodies or derivatives thereof are known in the art and can be used to generate target molecules which are bound by the peptide.

The most preferred peptide-target molecule pair of the present invention is the peptide identified by SEQ ID NO: 13 and the target molecule identified by the sequence of SEQ ID NO: 7.

The recombinant herpesvirus of the present invention may, in addition to the chimeric gH, comprise a modified gD glycoprotein, as disclosed in WO 2009/144755, herein incorporated by reference, but not limited to those types of modifications. A modified gD carries a modification for retargeting the recombinant herpesvirus to unwanted cells such as diseased cells such as tumor cells for elimination of such cells. Thus, gD may comprise additional polypeptide sequences that readdress the tropism of the herpesvirus to selected receptors of choice, e.g. to receptors on diseased cells such as the HER2 receptor. In addition, the modified gD may carry a deletion of the amino acid portion 6 to 38 that detarget herpesvirus tropism from the natural receptors Nectin-1 and HVEM. Alternatively, a modified gD may carry other modifications for detargeting. Modification of gD occurs by fusing to or inserting into gD heterologous polypeptide ligands that are capable of binding to a target molecule naturally present on a diseased cell which should be eliminated. A preferred ligand is an scFv directed to HER2 for eliminating tumor cells which express HER2. The recombinant herpesvirus of the present invention may, in addition to the chimeric gH, comprise a modified gB glycoprotein which is modified to comprise a heterologous polypeptide ligand and to retarget the recombinant herpesvirus to unwanted cells such as diseased cells such as tumor cells for elimination of such cells. The recombinant herpesvirus of the present invention may, in addition to the chimeric gH, comprise a modified gD and/or a modified gB glycoprotein. Modification of gH serves for the propagation and production of the recombinant herpesvirus in vitro in cell culture via binding of the recombinant herpesvirus to a target molecule present on the cell in cell culture, whereas modification of the gD and/or gB serves for the killing of unwanted cells such as diseased cells such as tumor cells via binding of the recombinant herpesvirus to a target molecule present on the unwanted cells.

The term "diseased cell", as used herein, refers to a cell which negatively influences an organism and is, therefore, not wanted. The eradication of such a cell is desired, as its killing may be live-saving or enhances the health of an organism. In a preferred embodiment, the diseased cell is characterized by an abnormal growth, more preferably the cell is a tumor cell. In an alternative preferred embodiment, the cell is an infected cell such as a chronically infected cell, a degenerative disorder-associated cell or a senescent cell.

In case of a tumor cell, the underlying disease is a tumor, preferably selected from the group consisting of adrenal cancer, anal cancer, bile duct cancer, bladder cancer, bone cancer, brain/CNS tumors, breast cancer, cancer of unknown primary treatment, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, liver cancer, lung cancer, lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer, small intestine cancer, stomach cancer, testicular cancer, thymus cancer, thyroid cancer, uterine sarcoma, vaginal cancer, vulvar cancer, Waldnstrom macroglobulinemia, and Wilms tumor.

Preferred tumor diseases are HER2-positive cancers (like breast cancer, ovary cancer, stomach cancer, lung cancer, head and neck cancer, osteosarcoma and glioblastoma multiforme), EGFR-positive cancers (like head and neck cancer, glioblastoma multiforme, non-small cell lung cancer, breast cancer, colorectal and pancreatic cancer), EGFR-vIII-positive cancers (like glioblastoma multiforme), PSMA-positive cancers (like prostate cancer), CD20+ positive lymphoma, and EBV related tumors such as B-cell lymphoproliferative disorders such as Burkitt's lymphoma, classic Hodgkin's lymphoma, and lymphomas arising in immunocompromised individuals (post-transplant and HIV-associated lymphoproliferative disorders), T-cell lymphoproliferative disorders, angioimmunoblastic T-cell lymphoma, extranodal nasal type natural killer/T-cell lymphoma.

In case of an infected cell, the underlying disease is an infectious disease, such as a chronic infectious disease, wherein the infectious agent may be a virus, a bacterium or a parasite. Examples are tuberculosis, malaria, chronic viral hepatitis (HBV, Hepatitis D virus and HCV), acquired immune deficiency syndrome (AIDS, caused by HIV, human immunodeficiency virus), EBV related disorders, or HCMV related disorders.

In case of a degenerative disorder-associated cell, the underlying disease may be Alzheimer's disease, amyotrophic lateral sclerosis (ALS), Lou Gehrig's Disease, osteoarthritis, atherosclerosis, Charcot Marie Tooth disease (CMT), chronic obstructive pulmonary disease (COPD), chronic traumatic encephalopathy, diabetes, ehlers-danlos syndrome, essential tremor, Friedreich's ataxia, huntington's disease, inflammatory bowel disease (IBD), keratoconus, keratoglobus, macular degeneration, marfan's syndrome, multiple sclerosis, multiple system atrophy, muscular dystrophy, Niemann Pick disease, osteoporosis, Parkinson's Disease, progressive supranuclear palsy, prostatitis, retinitis pigmentosa, rheumatoid arthritis, or Tay-Sachs disease. The term "degenerative disorder-associated cell" refers to a cell which is in relationship with the disorder, meaning that an alteration of the cell contributes to the development of the disease or the cell is altered as a consequence of the disease. Destroying the cell results in the treatment of the disease.

In case of a senescent cell, the underlying disease is a senescence-associated disease, such as (i) rare genetic diseases called progeroid syndromes, characterized by premature aging: Werner syndrome (WS), Bloom syndrome (BS), Rothmund-Thomson syndrome (RTS), Cockayne syndrome (CS), xeroderma pigmentosum (XP), trichothiodystrophy or Hutchinson-Gilford Progeria syndrome (HGPS) or (ii) common age related disorders, such as obesity, type 2 diabetes, sarcopenia, osteoarthritis, idiopathic pulmonary fibrosis, chronic obstructive pulmonary disease, cataracts, neurodegenerative diseases, systemic autoimmune diseases (systemic lupus erythematosus, rheumatoid arthritis, or Sjögren syndrome), or multiple sclerosis.

The recombinant herpesvirus of the present invention may be attenuated, for example by deletions in or alterations of genes known to attenuate virus virulence, such as the viral genes $y_1 34.5$, UL39, and/or ICP47. The term "attenuated" refers to a weakened or less virulent herpesvirus. Preferred is a conditional attenuation, wherein the attenuation affects only non-diseased cells. More preferred, only the diseased cells such as tumor cells are affected by the full virulence of the herpesvirus. A conditional attenuation can be achieved, for example, by the substitution of the promoter region of the $y_1 34.5$, UL39 and/or ICP47 gene with a promoter of a human gene that is exclusively expressed in diseased cells (e.g. the survivin promoter in tumor cells). Further modifications for a conditional attenuation may include the substitution of regulatory regions responsible for the transcription of IE genes (immediate early genes) like the ICP-4 promoter region with promoter regions of genes exclusively expressed in diseased cells (e.g. the survivin promoter). This change will result in a replication conditional HSV, which is able to replicate in diseased cells but not in normal cells. Additional modification of the virus may include the insertion of sequence elements responsive to microRNAs (miRs), which are abundant in normal but not tumor cells, into the 3' untranslated region of essential HSV genes like ICP4. The result will be again a virus that is replication incompetent only in normal cells.

The recombinant herpesvirus of the present invention may, furthermore, encode one or more molecule(s) that stimulate(s) the host immune response against a cell, preferably a diseased cell, as defined above. A molecule that stimulates the host immune response is also termed "immunotherapy molecule". Thus, the recombinant herpesvirus of the present invention may be a combined oncolytic and immunotherapeutic virus. An immunotherapeutic virus is a virus that encodes molecules that boost the host immune response to a cell, i.e. that stimulate the host immune response so as to be directed against a cell. An example of such a virus is T-VEC (Liu et al., 2003).

Immunotherapy molecules enable the recombinant virus, besides the modification of glycoproteins for retargeting the herpesvirus to diseased cells for killing them, to stimulate a subject's immune system in a specific or unspecific manner. Expression of immunotherapy molecules by the recombinant virus in a subject can induce an immune response which finally results in the killing of diseased cells. Immunotherapy may act specifically wherein the immunotherapy molecules stimulate the subject's immune system against one or some specific antigen(s) present on (a) cell(s). For example, an immunotherapy molecule may be an antibody which is directed against a specific cell surface receptor, e.g. CD20, CD274, and CD279. Once bound to an antigen, antibodies can induce antibody-dependent cell-mediated cytotoxicity, activate the complement system, or prevent a receptor from interacting with its ligand. All that can lead to cell death. Preferred cells are tumor cells. This technique is known and approved in the art. There are multiple antibodies which are approved to treat cancer, including Alemtuzumab, Ipilimumab, Nivolumab, Ofatumumab, and Rituximab. Alternatively, the immunotherapy molecule can act nonspecifically by stimulating the subject's immune system. Examples of immunotherapy molecules are inter alias cytokines, chemokines or immune checkpoint regulators. For example, some cytokines have the ability to enhance antitumor activity and can be used as passive cancer treatments. The use of cytokines as immunotherapy molecules is known in the art. Examples of cytokines are GM-CSF, interleukin-2, interleukin-12, or interferon-α. GM-CSF is used, for example in the treatment of hormone-refractory prostate cancer or leukemia. Interleukin-2 is used, for example, in the treatment of malignant melanoma and renal cell carcinoma.IL-12 is used in the experimental treatment of glioblastoma. Interferon-α is, for example, used in the treatment of hairy-cell leukemia, AIDS-related Kaposi's sarcoma, follicular lymphoma, chronic myeloid leukemia and malignant melanoma.

In a second aspect, the present invention provides a pharmaceutical composition comprising the herpesvirus of the present invention and a pharmaceutically acceptable carrier, optionally additionally comprising one or more molecule(s) that stimulate(s) the host immune response against a cell, preferably a diseased cell, as defined above. The recombinant herpesvirus of the present invention can be used as a medicament. For the production of the medicament the herpesvirus has to be in a pharmaceutical dosage form comprising the recombinant herpesvirus of the present invention and a mixture of ingredients such as pharmaceutically acceptable carriers which provide desirable characteristics. The pharmaceutical composition comprises one or more suitable pharmaceutically acceptable carrier which is/are known to those skilled in the art. The pharmaceutical composition may additionally comprise one or more molecule(s) that stimulate(s) the host immune response against a cell. The definition of a molecule that stimulates the host immune response against a cell is referred to above under the first aspect of the present invention.

The pharmaceutical composition can be manufactured for systemic, nasal, parenteral, vaginal, topic, vaginal, intratumoral administration. Parental administration includes subcutaneous, intracutaneous, intramuscular, intravenous or intraperitoneal administration.

The pharmaceutical composition can be formulated as various dosage forms including solid dosage forms for oral administration such as capsules, tablets, pills, powders and granules, liquid dosage forms for oral administration such as pharmaceutically acceptable emulsions, microemulsions, solutions, suspensions, syrups and elixirs, injectable preparations, for example, sterile injectable aqueous or oleaginous suspensions, compositions for rectal or vaginal administration, preferably suppositories, and dosage forms for topical or transdermal administration such as ointments, pastes, creams, lotions, gels, powders, solutions, sprays, inhalants or patches.

The specific therapeutically effective dose level for any particular subject will depend upon a variety of factors including the activity of the recombinant herpesvirus of the present invention, the dosage form, the age, body weight and sex of the subject, the duration of the treatment and like factors well known in the medical arts.

The total dose of the compounds of this invention administered to a subject in single or in multiple doses may be in amounts, for example, from $10^3$ to $10^{10}$. Single dose compositions may contain such amounts or submultiples thereof to make up the daily dose. The dosages of the recombinant herpesvirus may be defined as the number of plaque forming unit (pfu). Examples of dosages include $10^3$, $10^4$, $10^5$, $10^6$, $10^7$, $10^8$, $10^9$, or $10^{10}$.

The recombinant herpesvirus of the present invention may serve to treat diseases in which diseased cells express specific target molecules on their surface, so that they are accessible from the outside of the cell, which target molecules are not produced by a normal cell or are produced by the normal cell to a lower degree. The normal cell may be the respective normal cell. "Respective" means that the diseased and normal cells are of the same origin, however, cells develop into diseased cells due to disease-generating influences, whereas other cells of same origin remain healthy.

In a third aspect, the present invention provides the herpesvirus of the present invention, optionally in combination with one or more molecule(s) that stimulate(s) the host immune response against a cell, preferably a diseased cell, for use in the treatment of a tumor, infection, degenerative disorder or senescence-associated disease. The recombinant herpesvirus of the present invention and the molecule(s) that stimulate(s) the host immune response against a cell can be present within the same pharmaceutical composition or within different pharmaceutical compositions. If they are present in different pharmaceutical compositions, they may be administered simultaneously, or subsequently, either the herpesvirus before the molecule or the molecule before the herpesvirus. The herpesvirus or the molecule may be administered at different frequencies and/or time points. However, a combined treatment comprises that the herpesvirus and the molecule are administered at time intervals and/or time points that allow the simultaneous treatment of the disease.

The present invention also discloses a method of treating a subject having a tumor, infection, degenerative disorder or senescence-associated disorder by administering a pharmaceutically effective amount of the recombinant herpesvirus of the present invention.

The recombinant herpesvirus of the present invention may be administered to a subject in combination with further treatments which stimulate the host immune response against a cell, preferably a diseased cell, and/or serve to treat the specific disease of the subject. Such further treatments may include other drugs, chemotherapy, radiotherapy, immunotherapy, combined virotherapy etc.

The present invention also discloses the use of the herpesvirus of the present invention, optionally in combination with one or more molecule(s) that stimulate(s) the host immune response against a cell, preferably a diseased cell, for the preparation of a pharmaceutical composition for the treatment of a tumor, infection, degenerative disorder or senescence-associated disease.

The subjects which are treated by the recombinant herpesvirus of the present invention are preferably humans.

In a forth aspect, the present invention provides a nucleic acid molecule comprising a nucleic acid coding for the chimeric gH of the present invention having fused or inserted the peptide, preferably the part of the GCN4 yeast transcription factor as comprised by SEQ ID NO: 13, more preferably the sequence of SEQ ID NO: 13. The nucleic acid molecule may be the genome of the recombinant herpesvirus of the present invention or a part thereof. Preferably, the nucleic acid molecule encodes the precursor form of the chimeric gH including the signal sequence of the gH glycoprotein. If the chimeric gH was engineered to harbor the peptide to its N-terminal amino acid, the corresponding nucleic acid has the nucleic acid sequence of the peptide inserted between the last amino acid of the signal sequence and the first amino acid of the mature protein.

In a fifth aspect, the present invention provides a vector comprising the nucleic acid molecule. Suitable vectors are known in the art and include plasmids, cosmids, artificial chromosomes (e.g. bacterial, yeast or human), bacteriophages, viral vectors (retroviruses, lentiviruses, adenoviruses, adeno-associated viruses), in particular baculovirus vector, or nano-engineered substances (e.g. ormosils). In one embodiment, the vector is modified, in particular by a deletion, insertion and/or mutation of one or more nucleic acid bases, such that its virulence is attenuated, preferably in case of a viral vector, or that it replicates conditionally in diseased cells but not in non-diseased cells. For example, deletion of one or both copies of the $\gamma_1 34.5$ gene, the UL39 gene, the ICP47 gene results in attenuation of the virus. Attenuation or attenuated refers to weakened or less virulent virus.

Moreover, the substitution of the promoter region of the $\gamma_1 34.5$ gene with a promoter of a human gene that is exclusively expressed in diseased cells, e.g. tumor cells (e.g. survivin promoter in tumor cells), which will result in an attenuated phenotype in non-diseased cells and non-attenuated phenotype in diseased cells, is included. Further modifications may include the substitution of regulatory regions responsible for the transcription of IE genes like the ICP-4 promoter region with promoters of genes exclusively expressed in diseased cells (e.g. survivin promoter). This change will produce a replication conditional herpesvirus, able to replicate in diseased cells but not in normal cells. Cell culture cells for propagation of the virus progeny will provide high levels of specific promoter activating proteins to allow for the production of high virus yields.

In a sixth aspect, the present invention provides a polypeptide comprising the chimeric gH having fused or inserted the peptide, preferably the part of the GCN4 yeast transcription factor as comprised by SEQ ID NO: 13, more preferably the sequence of SEQ ID NO: 13.

In a seventh aspect, the present invention provides a cell comprising the recombinant herpesvirus of the present invention, the nucleic acid molecule of the present invention, the vector of the present invention, or the polypeptide of the present invention.

In an embodiment thereof, the cell is a cultured cell suitable for growth of herpesvirus, more preferably a cell line approved for growth of herpesvirus, still more preferably a Vero, 293, 293T, HEp-2, HeLa, BHK, or RS cell, most preferably a Vero cell.

In an eighth aspect or in an embodiment of the seventh aspect, the present invention provides a cell, wherein the cell comprises an artificial molecule capable of binding to the peptide comprised by the recombinant herpesvirus of the present invention, preferably to a part of the GCN4 yeast transcription factor, most preferably to the part of the GCN4 yeast transcription factor as comprised by SEQ ID NO: 13, accessible on the surface of the cell, preferably wherein the artificial molecule is an antibody, more preferably an antibody derivative, still more preferably an scFv, still more preferably an scFv capable of binding a part of the GCN4 yeast transcription factor, still more preferably an scFv capable of binding to the part of the GCN4 yeast transcription factor as comprised by SEQ ID NO: 13, still more preferably the scFv as comprised by SEQ ID NO: 5, most preferably the molecule identified by the sequence of SEQ ID NO: 7.

The term "cell", as referred to herein, is any cell which carries the target molecule, which can be infected by the recombinant herpesvirus of the present invention and which can produce the herpesvirus. As propagation of the herpesvirus shall be avoided in diseased cells, so as to avoid the introduction of material such as DNA, RNA and/or protein of diseased cells such as tumor cells in humans, the cell for producing the herpesvirus is a safe cell which does not produce material which may be harmful if present in humans, e.g. a non-diseased cell. The cell may be present as a cell line. Preferably, the cell is a cultured cell suitable for growth of herpesvirus, still more preferably the cell is a cell line approved for herpesvirus growth and still more preferably the cell is Vero, 293, 293T, HEp-2, HeLa, BHK, or RS cell, whereby the Vero cell is particularly preferred. The cell may be modified to express an artificial target molecule or to bind an artificial target molecule. More preferably, the cell comprises as the target molecule an antibody derivative, still more preferably an scFv, still more preferably an scFv capable of binding to a part of the GCN4 yeast transcription factor, still more preferably an scFv capable of binding to a part of the GCN4 yeast transcription factor as comprised by SEQ ID NO: 13, still more preferably an scFv as comprised by SEQ ID NO: 5, and most preferably the molecule identified by the sequence of SEQ ID NO: 7.

A "cultured" cell is a cell which is present in an in vitro cell culture which is maintained and propagated, as known in the art. Cultured cells are grown under controlled conditions, generally outside of their natural environment. Usually, cultured cells are derived from multicellular eukaryotes, especially animal cells. "A cell line approved for growth of herpesvirus" is meant to include any cell line which has been already shown that it can be infected by a herpesvirus, i.e. the virus enters the cell and is able to propagate and produce the virus. A cell line is a population of cells descended from a single cell and containing the same genetic composition. Preferred cells for propagation and production of the recombinant herpesvirus are Vero, 293, 293T, HEp-2, HeLa, BHK, or RS cells.

In a ninth aspect, the present invention provides an in-vitro method for producing a recombinant herpesvirus in a cell using the herpesvirus of the present invention, wherein the cell comprises an artificial molecule capable of binding to the peptide comprised by the recombinant herpesvirus of the present invention, preferably to a part of the GCN4 yeast transcription factor, most preferably to the part of the GCN4 yeast transcription factor as comprised by SEQ ID NO: 13, accessible on the surface of the cell, preferably wherein the artificial molecule is an antibody, more preferably an antibody derivative, still more preferably an scFv, still more preferably an scFv capable of binding a part of the GCN4 yeast transcription factor, still more preferably an scFv capable of binding to the part of the GCN4 yeast transcription factor as comprised by SEQ ID NO: 13, still more preferably the scFv as comprised by SEQ ID NO: 5, most preferably the molecule identified by the sequence of SEQ ID NO: 7.

The most preferred cell of the present invention is the Vero-GCN4 cell line which expresses as target molecule the molecule with the sequence of SEQ ID NO: 7 comprising the scFv capable of binding to the GCN4 peptide as identified by SEQ ID NO: 13. The Vero-GCN4 cell line serves inter alia the purpose of enabling the cultivation of herpesvirus recombinants retargeted to HER2-positive cells, and detargeted from natural herpesvirus receptors. Because HER2 is an oncogene, and the HER2-positive cells are cancer cells, it is advisable to avoid the growth of oncolytic herpesvirus recombinants destined to human use in cancer cells, in order to avoid the possible, accidental introduction of tumor-derived material (DNA, RNA, proteins) in humans. The rationale for the construction of the Vero-GCN4 cell line, and the companion HER2-retargeted herpesvirus was as follows. Vero-GCN4 cells express an artificial receptor made of a scFv to the peptide GCN4, fused to extracellular domains 2 and 3, transmembrane (TM), and C-tail of nectin1. Conversely, the HER2 retargeted herpesvirus expresses the GCN4 peptide in one of the envelope glycoproteins. In view of this, the recombinant virus is simultaneously retargeted to HER2 (in order to infect cancer cells) and to GCN4 peptide (in order to infect the Vero-GCN4 cell line, for virus growth and production). In the example system described below, the recombinant HSV named R-VG213 carries the scFv to HER2 fused in gD, in place of AA 6-38 (which are deleted from the final virus) and also carries the GCN4 peptide fused to gH, between AA 23 and 24.

Suitable techniques and conditions for growing herpesvirus in a cell are well known in the art (Florence et al., 1992; Peterson and Goyal, 1988) and include incubating the herpesvirus with the cell and recovering the herpesvirus from the medium of the infected cell culture.

FIGURES

FIG. 1 Schematic drawing of the chimeric scFv to GCN4—Nectin receptor. The receptor presents N-terminal leader peptide and HA tag sequence, followed by the scFv to GCN4, placed between two short linker, GA and GSGA linker. The second part of the molecule corresponds to human Nectin-1 (PVRL1) residues Met143 to Val517 comprising the Nectin-1 extracellular domains 2 and 3, the TM segment and the intracellular cytoplasmic tail.

Figure 2:
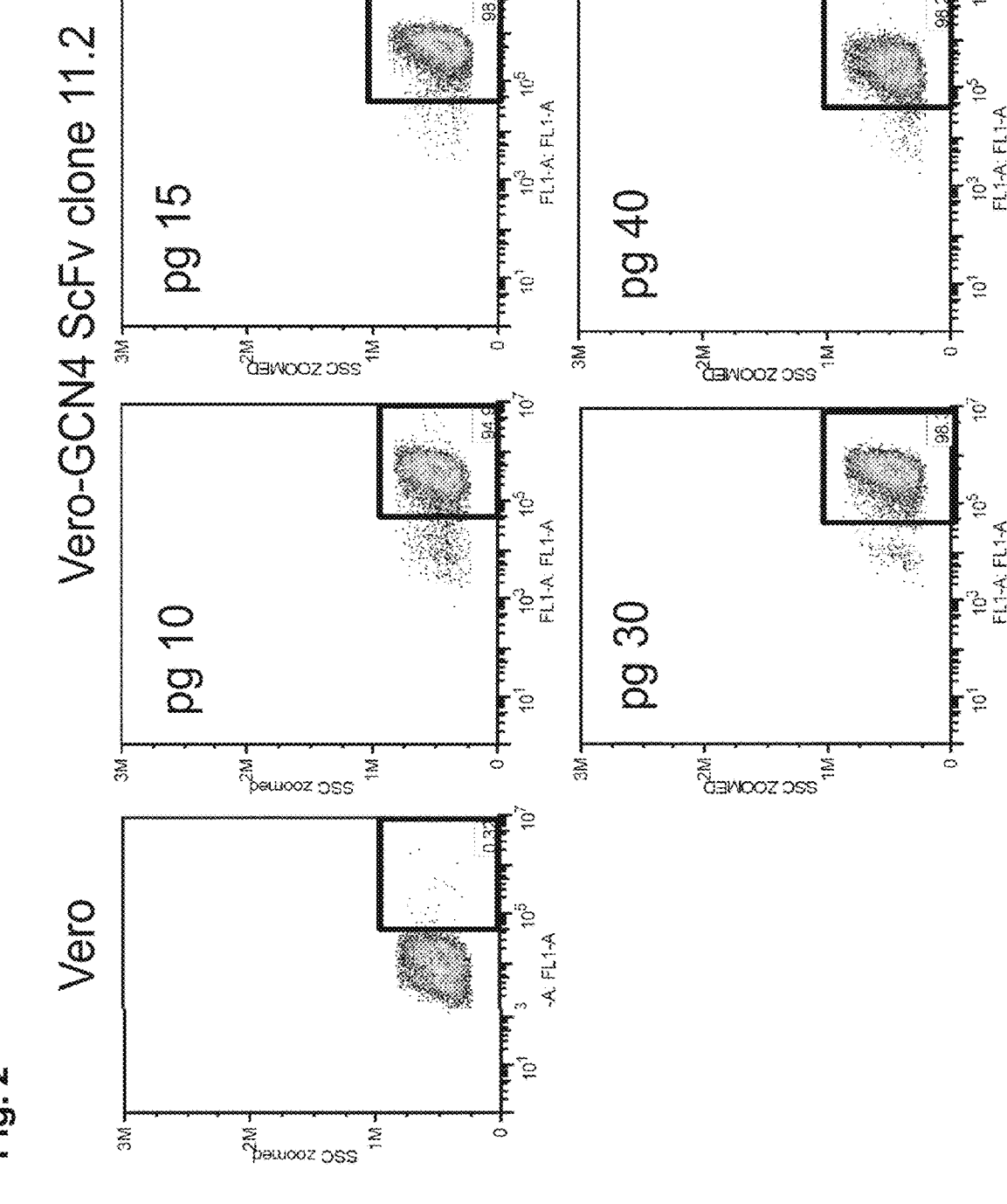

FIG. 2 Stability of Vero-GCN4 positive cells. The expression of the scFv GCN4-Nectin receptor was analyzed by FACS by means of Mab to HA tag. Diagrams show the percentage positive cells from Vero-GCN4 clone 11.2 cells at passages 10, 15, 30, 40. Result: the expression of the artificial receptor remained stable after 40 consecutive passages.

Figure 3:
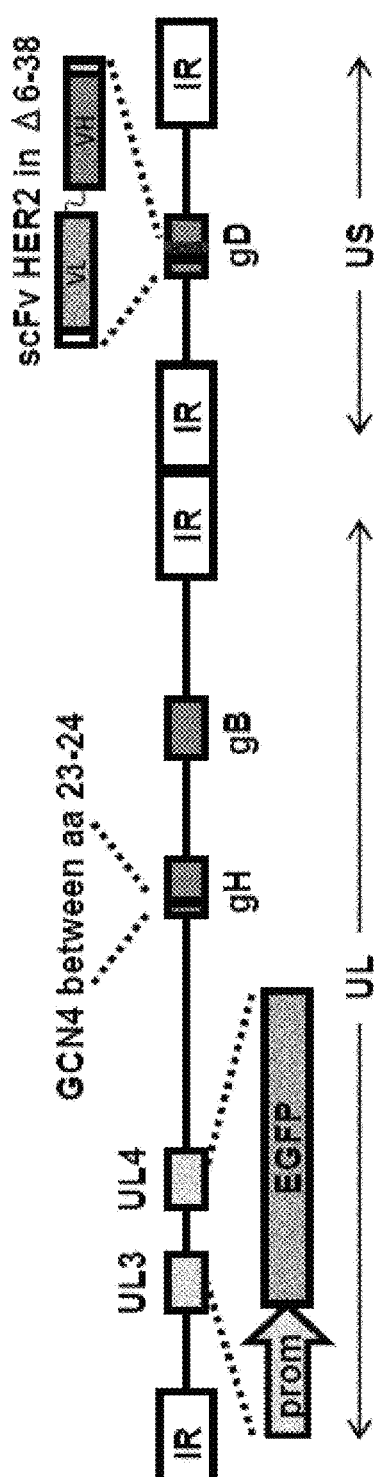

FIG. 3 Genome organization of R-VG213. Sequence arrangement of HSV-1 genome shows the inverted repeat sequences as rectangular boxes. The scFv-HER2 sequence (VL-linker-VH) is inserted in position Δ6-38 of gD, bracketed by upstream and downstream Gly-Ser linkers. LOX-P-bracketed p-Belo-BAC and EGFP sequences are inserted between UL3-UL4 region. The sequence encoding the GCN4 peptide is engineered in gH, at AA position 23-24.

Figure 4:
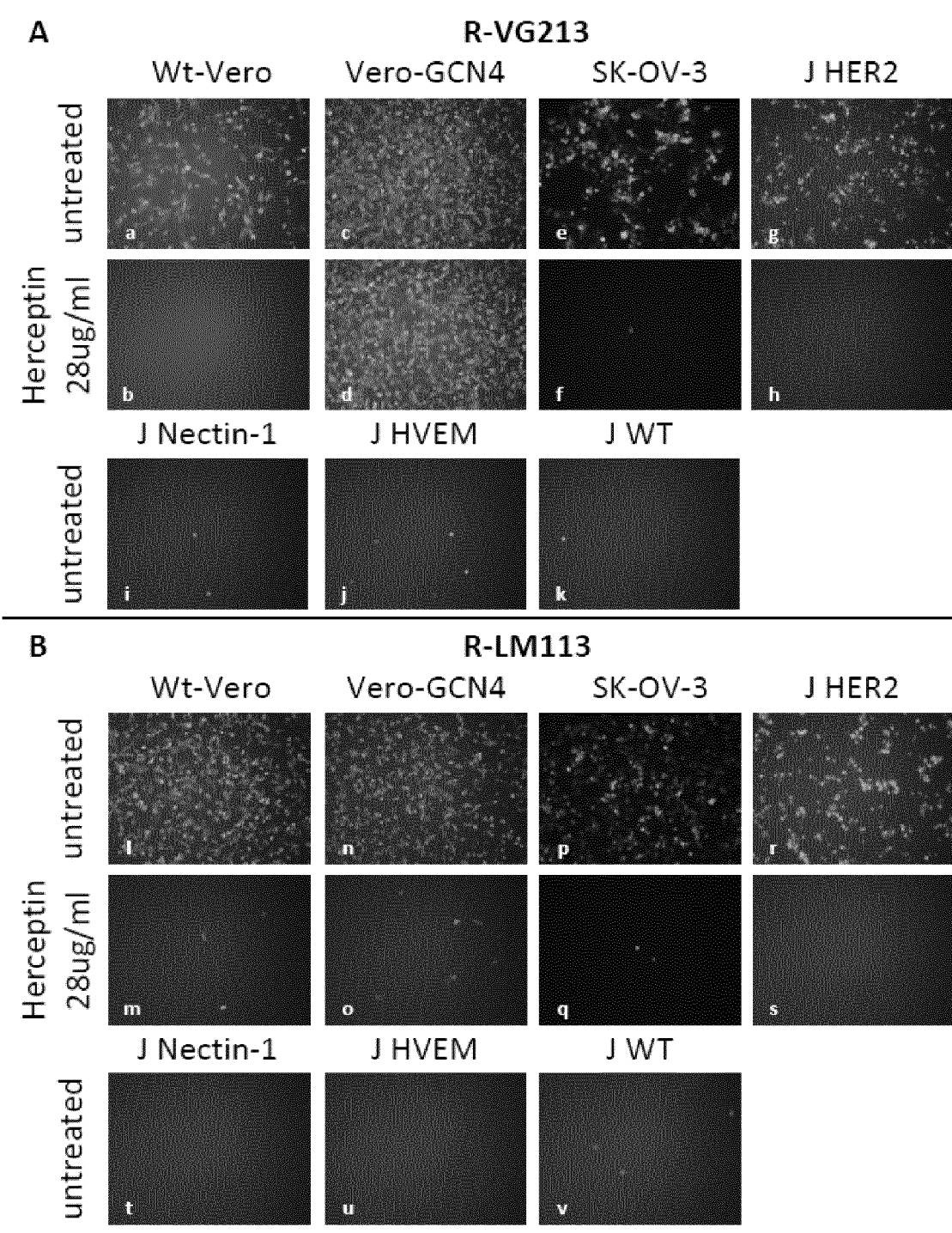

FIG. 4 Tropism of R-VG213 vs R-LM1 13. J cells express no receptor for wt-HSV. J-HER2, J-Nectin1, J-HVEM only express the indicated receptor. The indicated cells were infected with R-VG213 (FIG. 4A; panel a-k) or R-LM1 13 (FIG. 4B; panel l-v) and monitored for EGFP by fluorescence microscopy. Cells in panel b,d,f,h, and m,o,q,s were infected in presence of Herceptin/Trastuzumab at neutralizing dose (28 pg/ml). R-VG213 infects both the Vero-GCN4 cells (c), and the HER2-positive cancer cell line SK-OV-3 (e), in addition to the J-HER2 cells (g); it also infects wt-Vero cells, which express a simian ortholog of HER2 (a). Herceptin inhibits R-VG213 infection of wt-Vero, SK-OV-3 and J-HER2 cells (b, f, h), but not of Vero-GCN4 cells (d). R-VG213 fails to infect J-nectin1, J-HVEM and wt-J cells (i, j, k). The parental R-LM1 13, which is retargeted to HER2, but not to GCN4 peptide, infects HER2-positive cells (l, n, p, r), and fails to infect Vero-GCN4 cells treated with Herceptin (o).

Figure 5:
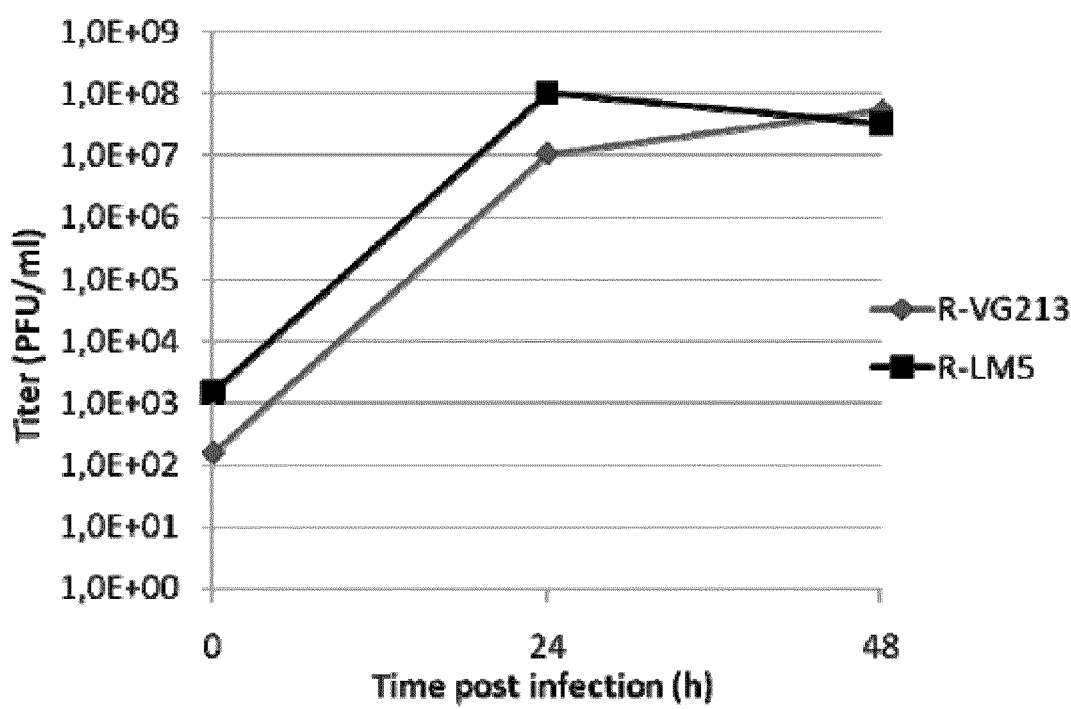

FIG. 5 Yield of R-VG213 and R-LM5 in Vero-GCN4 cells. The extent of R-VG213 replication in Vero-GCN4 cells was compared to that of R-LM5 virus. Vero-GCN4 cell were infected at MOI 0.1 PFU/cell with R-VG213 or R-LM5 (inoculum titrated in Vero-GCN4). Samples were collected at 0, 24 and 48 hours post infection and progeny virus was titrated in Vero GCN4 cells.

Figure 6:
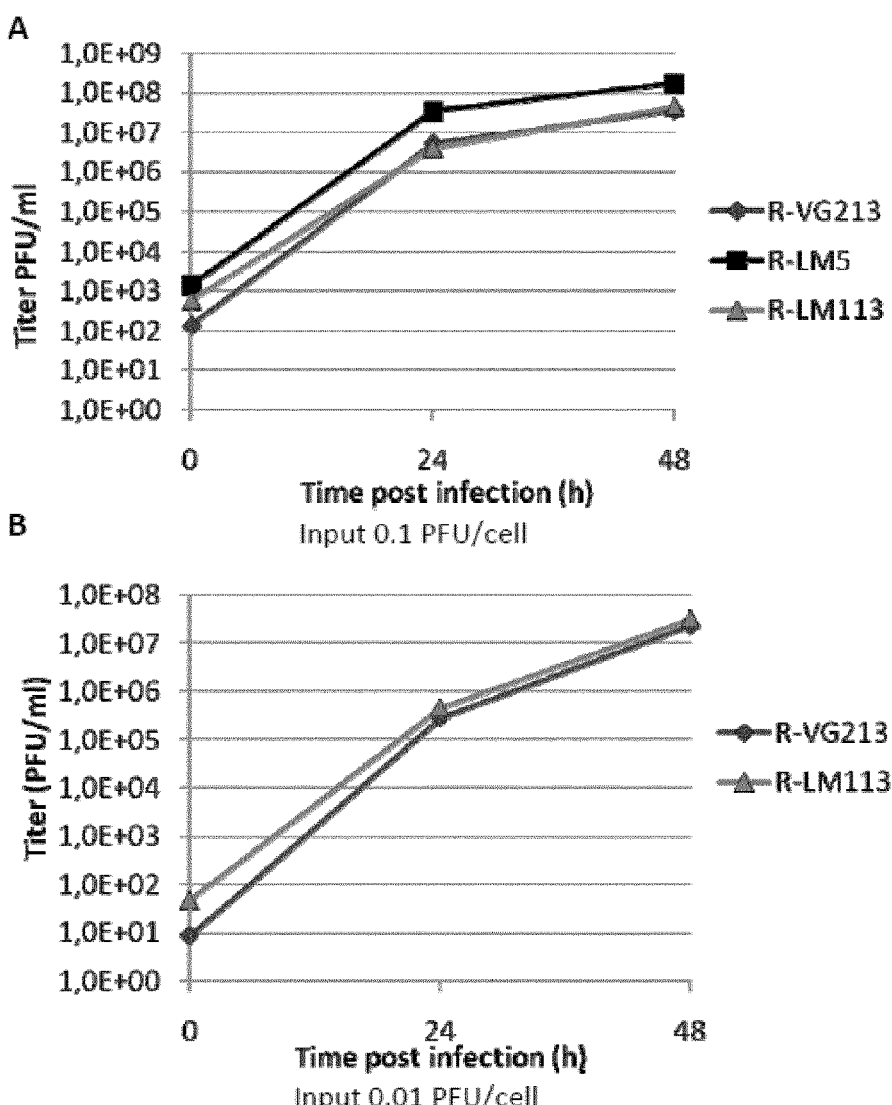
Figure 6:
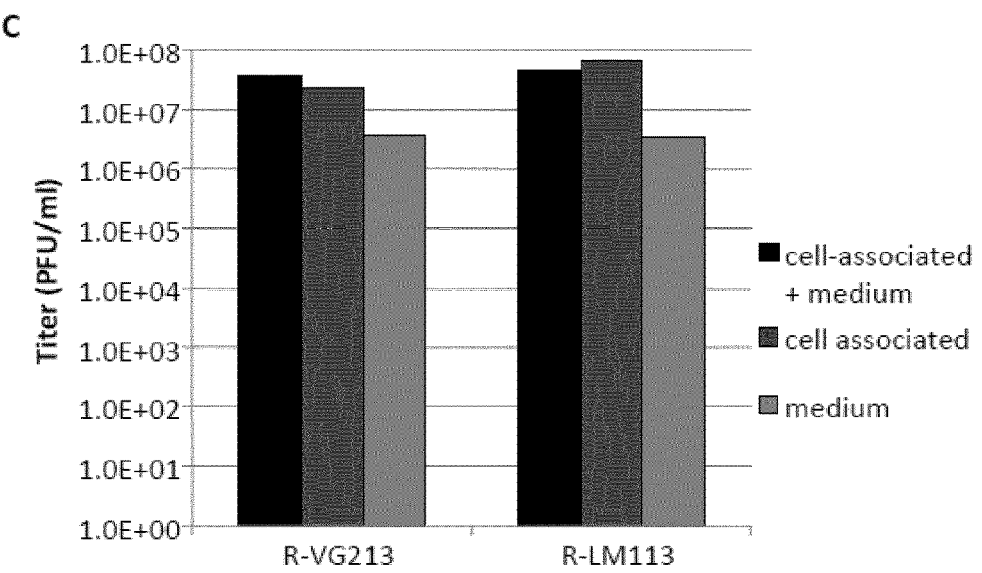

FIG. 6 Yield of R-VG213, R-LM113, R-LM5 in SK-OV-3 cells, and extent of progeny R-VG213 release in extracellular medium of SK-OV-3 cells. (A, B) The extent of R-VG213 replication in SK-OV-3 cells was compared to that of R-LM113 and wt-R-LM5 viruses. SK-OV-3 cells were infected at MOI 0.1 PFU/cell (panel A) or MOI 0.01 PFU/cell (panel B) (inocula were titrated in SK-OV-3 cells). Samples were collected at 0, 24 and 48 hours post infection and progeny virus was titrated in SK-OV-3 cells. (C) SK-OV-3 cells were infected with R-VG213 or R-LM113 at MOI 0.1 PFU/cell as in panel A (inoculum was titrated in SK-OV-3 cells). Samples were collected at 48 hours post infection and progeny virions released in the extracellular medium, present in the cell-associated fraction, or cell-associated plus medium were titrated.

Figure 7:
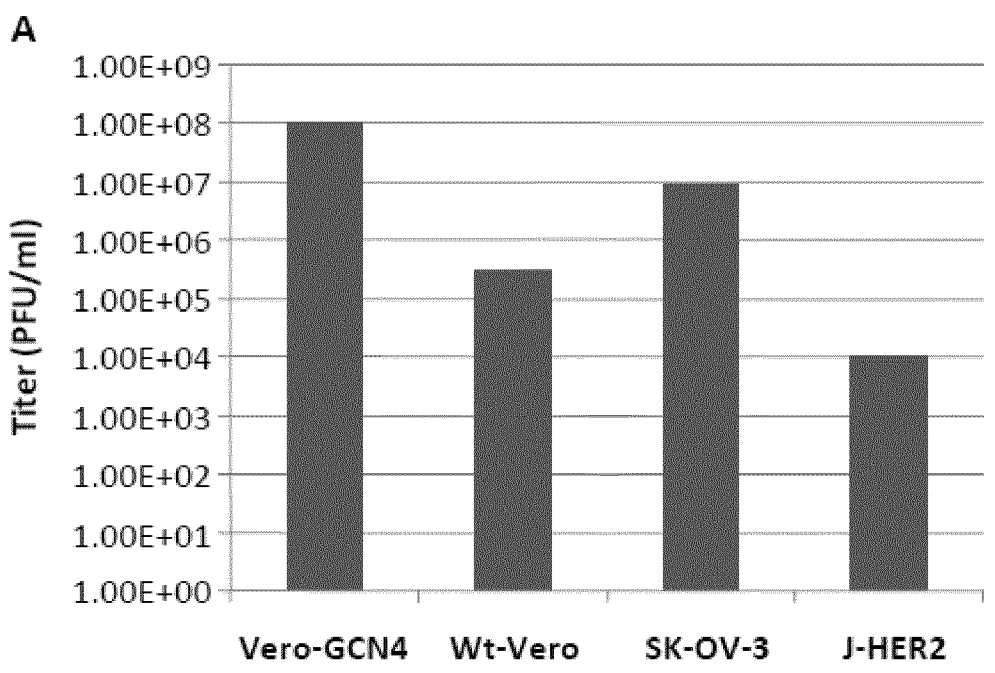
Figure 7:
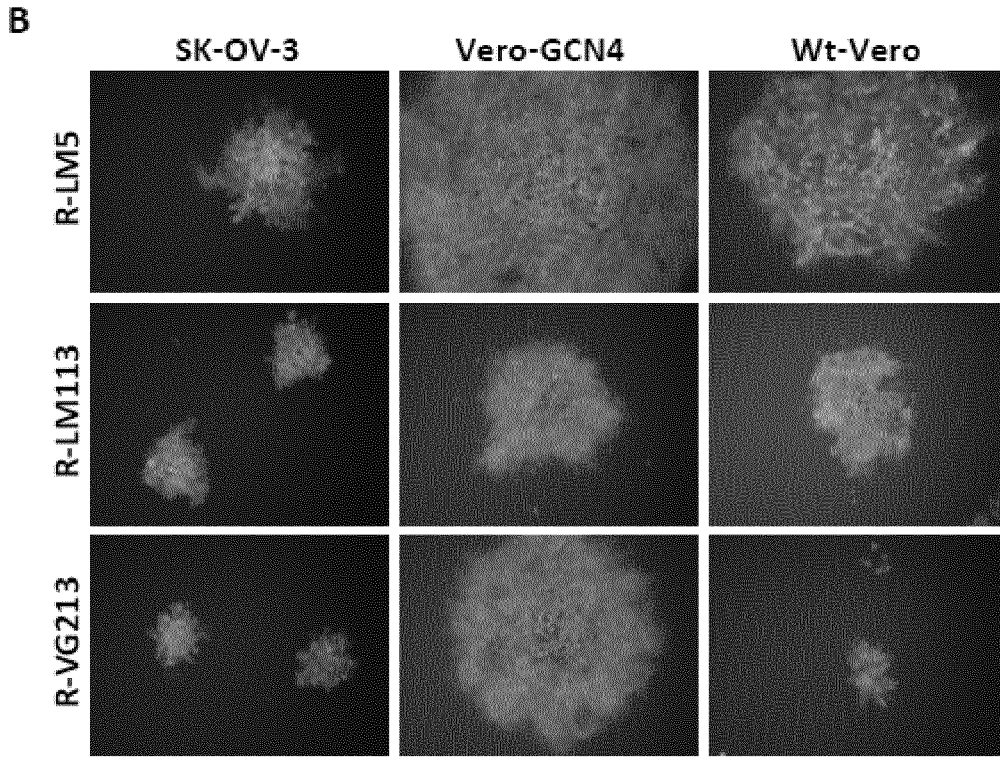

FIG. 7. Plating efficiency of R-VG213 in different cell lines. (A) Replicate aliquots of R-VG213 were plated in Vero-GCN4, wt-Vero, SK-OV-3 and J-HER2 cells and plaques were scored 3 days later. (B) Relative plaque size of R-VG213 in different cell lines. Replicate aliquots of R-VG213, R-LM113 and R-LM5 were plated in Vero-GCN4, Wt-Vero and SK-OV-3. Plaques were analyzed at fluorescence microscope 3 days post infection.

SEQUENCES

SEQ ID NO: 1: Amino acid sequence of gH wild type, precursor from HSV-1 (Human Herpesvirus 1 strain F, GenBank accession number: GU734771.1; gH encoded by positions 43741 to 46498).

SEQ ID NO: 2: Nucleotide sequence of chimeric gH-GCN4.

SEQ ID NO: 3: Amino acid sequence of gH precursor (SEQ ID NO: 1) having inserted the GCN4 peptide between amino acids 23 and 24, as encoded by the construct R-VG213. The GCN4 peptide is flanked by a Gly-Ser linker.

SEQ ID NO: 4: Nucleotide sequence of scFv to GCN4 peptide, optimized for human codon usage, and preceded by 96 nucleotide that form the signal sequence and the HA tag.

SEQ ID NO: 5: Amino acid sequence of scFv to GCN4 peptide (GenBank 1P4B), preceded by 32 AA that constitute the signal sequence and the HA tag. The sequence of the scFv to GCN4 peptide starts at amino acid 33.

SEQ ID NO: 6: Nucleotide sequence of scFv-GCN4 Nectin1 chimera.

SEQ ID NO: 7: Amino acid sequence of scFv-GCN4 Nectin1 chimera.

SEQ ID NO: 8: Primer gH5_galK_r

SEQ ID NO: 9: Primer gH6_galK_f

SEQ ID NO: 10: Primer galK_129_f

SEQ ID NO: 11: Primer galK_417_r

SEQ ID NO: 12: GCN4 peptide cassette—Nucleotide sequence of GCN4 peptide, bracketed by upstream and downstream GS linkers.

SEQ ID NO: 13: GCN4 peptide—Amino acid sequence of GCN4 peptide, bracketed by upstream and downstream GS linkers.

SEQ ID NO: 14: GCN4 epitope derived from *Saccharomyces cerevisiae* GCN4 mRNA (http://www.ncbi.nlm-.nih.gov/nuccore/15811626/).

SEQ ID NO: 15: Oligonucleotide GCN4gH_23_42_JB

SEQ ID NO: 16: Oligonucleotide GCN4gH_23_24_rB

SEQ ID NO: 17: Primer gH_ext_r pallino

SEQ ID NO: 18: Primer gH_2176_2200_f

SEQ ID NO: 19: GenBank accession number AJ585687.1 (gene encoding the GCN4 transcription factor)

SEQ ID NO: 20: amino acid sequence of GCN4 yeast transcription factor UniProtKB—P03069 (GCN4_YEAST)

EXAMPLES

Example 1: Generation of Vero-GCN4 Cell Line

The Vero-GCN4 cell line expresses an artificial chimeric receptor, made of a scFv to the GCN4 peptide (Zahnd et al., 2004), fused to Nectin-1. More in detail, a N-terminal signal peptide and HA tag sequence is present like in the pDIS-PLAY (Invitrogen) vector. This should ensure efficient and proper processing of the leader peptide. After the HA tag a short GA linker is present upstream of the scFv. The nucleotide and amino acid sequences of the scFv to GCN4, with sequence optimized for human codon usage, are reported in SEQ ID NOs: 4 and 5; included in those sequences are the signal peptide sequence and the sequence of the HA tag, which precede the sequences of the scFv. C-terminal to the scFv a short GSGA linker is present. The rest of the molecule corresponds to human Nectin-1 (PVRL1) residues Met143 to Val517 comprising the Nectin-1 extracellular domains 2 and 3, the TM segment and the intracellular cytoplasmic tail (FIG. 1). The chimera was synthesized in vitro by Gene Art, and cloned into pcDNA3.1—Hygro(+), resulting in plasmid scFv_GCN4_Nectin1 chimera, whose insert has the nucleotide sequence reported as SEQ ID NO: 6, and the amino acid sequence identified as SEQ ID NO: 7.

The DNA from plasmid scFv_GCN4_Nectin1 chimera was transfected into Vero cells (ATCC CCL-81™) by means of Lipofectamine 2000™. Vero cells expressing the artificial receptor to GCN4 peptide were selected by means of hygromycin (200 µg/ml), and subsequently sorted by means of magnetic beads (Miltenyi), in combination with Mab to HA tag. The sorted cells were subjected to single cell cloning in 96 well (0.5 cell/well).

Single clones were analysed by FACS for detection of expression of the scFv to GCN4 peptide by means of MAb to HA tag. The selected clone was 11.2.

Example 2: Stability of Vero-GCN4 Cell Line

The inventors ascertained that during serial passages of the Vero-GCN4 cell line, the expression of the artificial receptor remained stable after 40 consecutive passages (FIG. 2).

Example 3

Description of the HSV recombinant named R-VG213 (FIG. 3), which expresses a genetically modified gH carrying the GCN4 peptide, a gD carrying a single chain antibody (scFv) directed to HER2 (scFv-HER2), and eGFP as reporter gene.

Below is a description of the insertion of the sequence encoding the GCN4 peptide, between AA 23 and 24 of HSV gH. The insertion was carried out in the HSV recombinant named R-LM113, which expresses a scFv-HER2 in gD, in place of the deleted sequences AA 6-38. Specifically, the sequence encoding the GCN4 peptide was inserted between AA 23 and 24 of immature gH, corresponding to AA 5 and 6 of mature gH, after cleavage of the signal sequence, which encompasses AA 1-18. The starting genome was the BAC LM113, which carries scFv-HER2 in place of AA 6 to 38 of gD, LOX-P-bracketed pBeloBAC11 and eGFP sequences inserted between $U_L3$ and $U_L4$ of HSV-1 genome (Menotti et al., 2008). The engineering was performed by means of galK recombineering. In order to insert the GCN4 peptide in gH, the galK cassette with homology arms to gH was amplified by means of primers gH5_galK_r TCGTGGGGGGTTATTAT-TTTGGGCGTTGCGTGGGGTCAGGTC-CACGACTGGTC AGCACTGTCCTGCTCCTT (SEQ ID NO: 8) and gH6_galK_f ATGCGGTCCATGCCCAGGC-CATCCAAAAACCATGGGTCTGTCTGCTCAGTCC TGTTGACAATTAATCATCGGCA (SEQ ID NO: 9) using pGalK as template. This cassette was electroporated in SW102 bacteria carrying the BAC LM113. The recombinant clones carrying the galK cassette were selected on plates containing M63 medium (15 mM (NH$_4$)$_2$SO$_4$, 100 mM KH$_2$PO$_4$, 1.8 µg FeSO$_4$·H$_2$O, adjusted to pH7) supplemented with 1 mg/L D-biotin, 0.2% galactose, 45 mg/L L-leucine, 1 mM MgSO$_4$·7H$_2$O and 12 µg/ml chloramphenicol. In order to exclude galK false positive bacterial colonies, they were streaked also on MacConkey agar base plates supplemented with 1% galactose and 12 µg/ml chloramphenicol and checked by colony-PCR with primer galK_129_f ACAATCTCTGTTTGCCAACGCATTTGG (SEQ ID NO: 10) and galK_417_r CATTGCCGCTGAT-CACCATGTCCACGC (SEQ ID NO: 11). Next, the DNA fragment encoding the GCN4 peptide cassette, with nucleotide sequence identified as SEQ ID NO: 12, encoding the GCN4 peptide having the AA sequence identified as SEQ ID NO: 13, bracketed by upstream and downstream Gly-Ser linkers, and by homology arms to gH, was generated through the annealing and extension of synthetic oligonucleotides GCN4gH_23_42_fB TCGTGGGGGTTATTAT-TTTGGGCGTTGCGTGGGGTCAGGTCCACGACTGGG GATCCAAGAACTACCACCTG-GAGAACGAGGTGGCCAGACTGAAGAAGCTGG TGGGCAGC (SEQ ID NO: 15) and GCN4gH_23_24_rB ATGCGGTCCATGCCCAGGCCATCCAAAAAC-CATGGGTCTGTCTGCTCAGTGC TGCC-CACCAGCTTCTTCAGTCTGGC-CACCTCGTTCTCCAGGTGGTAGTTCTT GGATCC (SEQ ID NO: 16), which introduce a silent restriction site for the BamHI endonuclease, useful for screening of colonies by means of restriction analysis. The recombinant BAC R-VG-213 encodes the chimeric gH, whose nucleotide sequence is identified as SEQ ID NO: 2, and whose amino acid sequence is identified as SEQ ID NO: 3. The recombinant BAC R-VG213 bacterial clones were selected on plates containing M63 medium (see above) supplemented with 1 mg/L D-biotin, 0.2% deoxy-2-galactose, 0.2% glycerol, 45 mg/L L-leucine, 1 mM MgSO4·7H$_2$O and 12 µg/ml chloramphenicol. Bacterial colonies were checked for the presence of sequence of choice by means of colony PCR with primers gH_ext_r pallino GTTTCTTCCTTTTCCC-CACCCCACCCC (SEQ ID NO: 17) and gH_2176_2200_f CAGGTAGGTCTTCGGGATGTAAAGC (SEQ ID NO: 18).

To reconstitute the recombinant virus R-VG213, 500 ng of recombinant BAC DNA was transfected into the Vero-GCN4 cell line by means of Lipofectamine 2000™ (Life Technologies), and then grown in these cells. Virus growth was monitored by green fluorescence. The authenticity of the recombinants was verified by sequencing the entire gH and gD ORFs. Virus stocks were generated in Vero-GCN4 cells and titrated in Vero-GCN4 and SK-OV-3 cells.

Example 4: Double Tropism of R-VG213 for Vero-GCN4 and for HER2-Positive J-HER2 and SK-OV-3 Cells It has previously been shown that the insertion of scFv-HER2 in gD confers to the recombinant virus R-LM113 the ability to enter cells through the HER2 receptor, and that R-LM113 is detargeted from the natural gD receptors Nectin1 and HVEM, because of the deletion of the gD region between AA 6-38. To verify whether the insertion of the GCN4 peptide enables R-VG213 to infected the Vero-GCN4 cells, the inventors made use of Vero-GCN4 cell line and its wt counterpart, wt Vero. To verify that R-VG213 is still capable to infect through the HER2 receptor, the inventors made us of the J-HER2 cells, which express HER2 as the sole receptor, and of the HER2-positive cancer cells, SK-OV-3 cells. In addition, to verify that R-VG213 maintains the detargeting from nectin1 and HVEM, the inventors made us of J-Nectin1 and J-HVEM, which express only the indicated receptor. Cells were infected with R-LM213 (FIG. 4 panel A) and with R-LM113 (FIG. 4 panel B). Where indicated, infection was carried out in the presence of MAb to HER2, named herceptin, at the concentration of 28 µg/ml. Infection was carried out at 1 PFU/cell, and was monitored 24 hours later by fluorescence microscopy. As shown in FIG. 4 A, R-VG213 infected Vero-GCN4 cells; this infection was not inhibited by herceptin, indicating that it occurred through the GCN4 receptor. The infection seen in wt Vero was inhibited by herceptin, indication that it occurs through the simian ortholog of HER2. R-VG213 infected SK-OV-3 and J-HER2 cells, in a fashion inhibited by herceptin, i.e. HER2-dependent. As expected, R-VG213 did not infect J-nectin1, J-HVEM, and wt-J cells indicating that it preserved the detargeted phenotype. The infection of Vero-GCN4 cells with R-VG213 is in sharp contrast with that of R-LM113, which infects cells solely through HER2 (FIG. 4 B).

Example 5: Extent of R-VG213 Replication in Vero-GCN4 Cells, as Compared to that of the Wt-Virus R-LM5

The inventors compared the extent of replication in Vero-GCN4 cells of R-VG213 to that of R-LM5, a virus carrying wt gH and wt-gD. Vero-GCN4 cell were infected at MOI 0.1 PFU/cell with R-VG213 or R-LM5 (inoculum titrated in VERO-GCN4 cells), for 90 min at 37° C. Unabsorbed virus was inactivated by means of an acidic wash (40 mM citric acid, 10 mM KCl, 135 mM NaCl [pH 3]). Replicate cultures were frozen at the indicated times (0, 24 and 48 h) after infection and the progeny was titrated in VERO-GCN4 cells. It can be seen from FIG. 5 that R.VG213 grew about one log less than R-LM5 at 24 h. At 48 h the extent of replication was undistinguishable.

Example 6: Replication of R-VG213 in SK-OV-3 Cells, in Comparison to R-LM113 and R-LM5, and Extent of Progeny R-VG213 Release in Extracellular Medium of SK-OV-3 Cells (A, B) The inventors compared the extent of replication of R-VG213 to that of the recombinant R-LM113, also retargeted to HER2 through the insertion of scFv-HER2 in gD, and of the wt R-LM5. Replication was measured in SK-OV-3 cells, which express HER2 and Nectin-1/HVEM as receptors. Replication was carried out at input MOI of 0.1 (panel A) or 0.01 (panel B) PFU/cell. Unabsorbed virus was inactivated by means of an acidic wash (40 mM citric acid, 10 mM KCl, 135 mM NaCl [pH 3]). Replicate cultures were frozen at the indicated times (0, 24 and 48 h) after infection and the progeny was titrated in SK-OV-3 cells. It can be seen from FIG. 6 A and B that R-VG213 replication could not be differentiated from that of its parent R-LM113, and about half log less than the wt R-LM5. (C). The inventors compared R-VG213 and R-LM113 with respect to the extent of progeny virus release to the extracellular medium of SK-OV-3 cells infected at 0.1 PFU/cell (experiment shown in panel A). At 48 h after infection, replicate cultures were either frozen as whole lysates plus medium (cell-associated+ medium), or medium and cell-associated fractions were separated and frozen. Progeny virus was titrated in SK-OV-3 cells. It can be seen that the efficiency of progeny release in the extracellular medium was very similar.

Example 7: Plating Efficiency of R-VG213 in Different Cell Lines

The inventors compared the ability of R-VG213 to form plaques in different cell lines, with respect to number of plaques (A), and to plaque size (B). (A) Replicate aliquots of R-VG213 were plated in Vero-GCN4, Wt-Vero, SK-OV-3 and J-HER2 cells and the number of plaques were scored 3 days later. It can be seen that the highest plating efficiency is reached in Vero-GCN4 cells. (B) Typical examples of relative plaque size of R-VG213 in different cells. Even by this parameter R-VG213 exhibits a large plaque phenotype in Vero-GCN4 cells.

Chowdary et al., 2010), one from the swine PrV (Backovic et al., 2012), also an alphaherpesvirus, and one from Epstein-Barr virus (Matsuura et al., 2010

REFERENCES

Abstract #P-28, 9th International conference on Oncolytic virus Therapeutics, Boston 2015

Arndt K. and Fin G. R., PNAS 1986, 83, 8516-8520

Backovic M. et al., PNAS, 2012, 107, 22635-22640

Chowdary T. K. et al., Nat Struct Mol Biol, 2010, 17, 882-888

Douglas J. T. et al., Nat Biotechnol, 1999, 17, 470-475

Florence G. et al., Virology: A Laboratory Manual, 1992, ISBN-13: 978-0121447304

Gatta V. et al., PLOS Pathogens, 2015, DOI: 10.1371/journal.ppat.1004907

Hope I. A. and Struhl K., EMBO J, 1987, 6, 2781-2784

Karlin S. and Altschul S. F., PNAS, 1990, 87, 2264-2268

Karlin S. and Altschul S. F., PNAS, 1993, 90, 5873-5877

Matsuura H. et al., PNAS, 2010, 107, 22641-22646

Menotti L, et al., J Virol, 2008, 82, 10153-10161; doi: 10.1128/JVI.01133-08. Epub 2008 Aug. 6.

Nakamura T. et al., Nat Biotechnol, 2005, 23, 209-214. Epub 2005 Jan. 30

Needleman S. B. and Wunsch C. D., J Mol Biol, 1970, 48, 443-453

Pearson W. R. and Lipman D. J., PNAS, 1988, 85, 2444-2448

Peterson R. B. and Goyal S. M., Comp Immunol Microbiol Infect Dis. 1988, 11, 93-98

Sandri-Goldin R. M. et al., Alpha Herpesviruses: Molecular and Cellular Biology, Caister Academic Press, 2006

Smith T. F. and Waterman M. S., Add APL Math, 1981, 2, 482-489

Zahnd C. et al., J Biol Chem 2004; 279, 18870-18877

The invention claimed is:

1. A recombinant herpesvirus comprising a peptide having a length of up to 274 amino acids, fused to or inserted into the N-terminal region of glycoprotein H (gH) present in the envelope of the herpesvirus, wherein said peptide comprises SEQ ID NOs: 13 or 14, wherein the herpesvirus can: (1) bind to a cell or bind to an artificial target molecule when expressed by the cell, (2) enter the cell, and/or (3) propagate within the cell, and wherein the target molecule is an antibody or antigen binding fragment thereof, or a scFv that binds the GCN4 yeast transcription factor.

2. The herpesvirus according to claim 1, wherein the peptide is inserted within the N-terminal region beginning between amino acids 19 to 23 and ending between amino acids 48 to 88 prior to insertion of the peptide.

3. The herpesvirus according to claim 1, wherein the peptide is inserted N-terminally of the H1A domain of gH.

4. The herpesvirus according to claim 1, wherein one or more gH amino acids of the N-terminal region are deleted.

5. The herpesvirus according to claim 1, wherein the target molecule is an scFv comprising SEQ ID NO: 5, or SEQ ID NO: 7.

6. The herpesvirus according to claim 1, wherein the herpesvirus comprises a gD which is modified to retarget the herpesvirus to a diseased cell or a gB which is modified to retarget the herpesvirus to a diseased cell.

7. The herpesvirus according to claim 1, wherein the herpesvirus encodes one or more molecule(s) that stimulate(s) the host immune response against a diseased cell.

8. A pharmaceutical composition comprising the herpesvirus according to claim 1 and a pharmaceutically acceptable carrier.

9. A nucleic acid molecule comprising a nucleic acid coding for the gH, as comprised by the recombinant herpesvirus according to claim 1, wherein the peptide has a length of up to 274 amino acids, fused to or inserted into the N-terminal region of gH present in the envelope of the herpesvirus, and wherein said peptide comprises SEQ ID NOs: 13 or 14.

10. A vector comprising the nucleic acid molecule of claim 9.

11. A polypeptide comprising the gH comprised in the recombinant herpesvirus according to claim 1, having fused or inserted the peptide.

12. An isolated cell comprising the herpesvirus according to claim 1.

13. The cell according to claim 12, wherein the cell is a cultured cell suitable for growth of herpesvirus.

14. An isolated cell comprising the nucleic acid molecule according to claim 9.

15. An isolated cell comprising the vector according to claim 10.

16. An isolated cell comprising the polypeptide according to claim 11.

17. The herpesvirus according to claim 1, wherein the peptide has a length of 12 to 29, 31 to 39, 41 to 49 or 51 to 200 amino acids.

18. The herpesvirus according to claim 1, wherein the peptide has a length of 12 to 20 amino acids.

19. The pharmaceutical composition of claim 8, further comprising one or more molecules that stimulate the host immune response against a cell.

* * * * *